United States Patent [19]

Reiners et al.

[11] Patent Number: 4,843,136

[45] Date of Patent: Jun. 27, 1989

[54] (METH)-ACRYLATES OF SILOXANES CONTAINING TRICYCLODECANE GROUPS

[75] Inventors: Jürgen Reiners, Leverkusen; Ottfried Schlak, Cologne; Wolfgang Podszun, Cologne; Jens Winkel, Cologne, all of Fed. Rep. of Germany

[73] Assignee: Bayer Aktiengesellschaft, Leverkusen, Fed. Rep. of Germany

[21] Appl. No.: 94,971

[22] Filed: Sep. 9, 1987

[30] Foreign Application Priority Data

Sep. 26, 1986 [DE] Fed. Rep. of Germany ....... 3632657
Sep. 26, 1986 [DE] Fed. Rep. of Germany ....... 3632792
Mar. 12, 1987 [JP] Japan ................... 3707908

[51] Int. Cl.$^4$ ................................ C08F 30/08
[52] U.S. Cl. ................... 526/279; 556/420; 556/440; 556/462; 528/26; 528/28; 528/32
[58] Field of Search ............... 556/420, 440, 462; 528/26, 28, 32; 526/279

[56] References Cited

U.S. PATENT DOCUMENTS 4,684,538 8/1987 Klemarczyk .............. 528/28
4,724,248 2/1988 Dexter ...................... 556/420
4,740,575 4/1988 Nguyen et al. ........... 528/28

Primary Examiner—Melvyn I. Marquis
Attorney, Agent, or Firm—Sprung Horn Kramer & Woods

[57] ABSTRACT

New (meth)-acrylates of siloxanes containing tricyclodecane groups having the formula

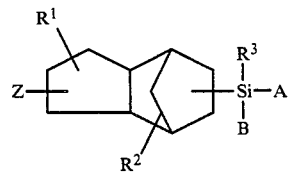

are prepared by reacting poly(hydroxymethyl-tricyclo [5.2.1.0$^{2,6}$]decanyl)siloxanes, or the alkylene oxide adducts thereof with (meth)acrylic acid or a derivative thereof or with an isocyanato (meth)acrylate.

These compounds can be employed as monomers to prepare polymers and dental materials.

9 Claims, No Drawings

(METH)-ACRYLATES OF SILOXANES CONTAINING TRICYCLODECANE GROUPS

The invention relates to (meth)-acrylates of siloxanes containing tricyclodecane groups, a process for the preparation of these, and their use as monomers in dental materials.

DE-A No. 2,922,932 discloses dental filling materials which are prepared from hydroly zates of 3-methacryloyloxypropyl-trialkoxysilanes.

DE-A No. 3,038,153 describes a prosthesis base material which is obtained from methyl methacrylate, a silane compound such as 3-methacryloyloxypropyl-triethoxysilane, and an unsaturated carboxylic acid.

However, the inadequate mechanical properties of the known materials made from polysiloxanes exclude their use in practice as a matrix in dental materials.

New (meth)-acrylates of siloxanes containing tricyclodecane groups, of the formula

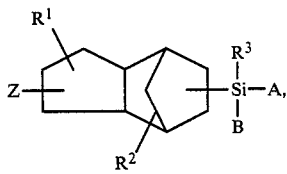

in which
R$^1$ and R$^2$ are identical or different and denote hydrogen, lower alkyl, halogen or trifluoromethyl,
R$^3$ denotes lower alkyl, cycloalkyl, cycloalkyl-alkyl or optionally substituted aryl or aralkyl,
Z represents the

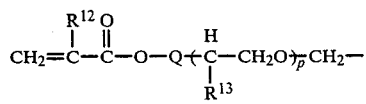

group, in which
R$^{12}$ and R$^{13}$ are identical or different and denote hydrogen or methyl,
P represents a number from 0 to 20 and
Q represents a single bond, or denotes a radical of the formula

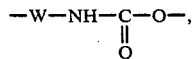

in which
W denotes an alkylene chain,
or denotes a radical of the formula

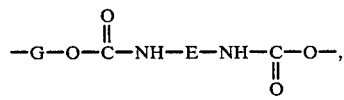

in which
E is a divalent, straight-chain or branched aliphatic radical having 2 to 24 carbon atoms, an aromatic radical having 6 to 26 carbon atoms, an araliphatic radical having 7 to 26 carbon atoms, or a cycloaliphatic radical having 6 to 26 carbon atoms, it being possible for the aliphatic, aromatic, araliphatic and/or cycloaliphatic radicals to contain 1 or 2 oxygen bridges, and it being possible for several of the aliphatic, aromatic, araliphatic and/or cycloaliphatic radicals to be connected via optionally substituted methylene groups, and
G denotes a divalent straight-chain or branched aliphatic hydrocarbon radical, having 3 to 15 carbon atoms, which may optionally contain 1 to 3 oxygen bridges and may optionally be substituted by 1 to 4 additional (meth)acryloyloxy radicals,
A represents a siloxane chain which comprises m structural elements of the formula

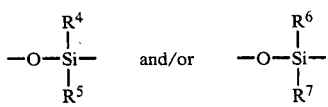

and the terminal group

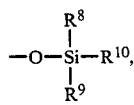

where
R$^4$, R$^5$, R$^6$, R$^7$, R$^8$ and R$^9$ are identical or different and denote lower alkyl, cycloalkyl, cycloalkylalkyl or optionally substituted aryl or aralkyl,
where the radicals R$^5$, R$^7$ and R$^8$ alternatively represent the

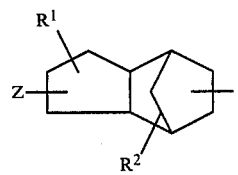

group, in which
R$^1$, R$^2$ and Z have the abovementioned meaning,
R$^{10}$ represents lower alkyl, and where the total number of structural elements m, independently of one another, represent a number from 0 to 600, and
B can have the same range of meanings as A, it being possible for the radicals R$^4$ to R$^{10}$ in chains A and B to be different, or represents lower alkyl,
have been found.

After polymerization, the new (meth)-acrylates of siloxanes containing tricyclodecane groups produce plastics which meet the practical demands of dental materials. In particular, they exhibit a very low polymerization shrinkage and excellent mechanical properties and high stability against physical and chemical degradation in the oral environment. At a low siloxane content, for example as disiloxane, the monomers surprisingly also exhibit a low viscosity.

In the context of the present invention, the substituents generally have the following meaning:

Lower alkyl can represent a straight-chain or branched alkyl radical having 1 to about 6 carbon atoms. Examples which may be mentioned are methyl, ethyl, n-propyl, iso-propyl, n-butyl, iso-butyl, n-pentyl, iso-pentyl, n-hexyl and iso-hexyl. Preferred lower alkyl radicals are methyl and ethyl.

Halogen can denote fluorine, chlorine, bromine or iodine, preferably fluorine or chlorine.

Cycloalkyl can represent a cyclic, preferably monocyclic, hydrocarbon radical having 5 to 7 carbon atoms. Examples which may be mentioned are cyclopentyl, cyclohexyl and cycloheptyl. Cyclopentyl and cyclohexyl are preferred.

Cycloalkyl-alkyl can represent a radical having 6 to 13 carbon atoms, it being possible for a straight-chain or branched alkyl radical ($C_1$ to $C_6$) to be substituted by a cycloalkyl radical ($C_5$ to $C_7$). Examples which may be mentioned are cyclohexylmethyl, 2-cyclohexyl-1-ethyl, cycloheptylmethyl and 2-cycloheptyl-1-ethyl. Cyclohexylmethyl and 2-cyclohexyl-1-ethyl are preferred.

Aryl can represent an aromatic hydrocarbon radical having 6 to 12 carbon atoms. Examples which may be mentioned are phenyl, naphthyl and biphenyl. Phenyl is preferred.

Aralkyl can represent a radical having 7 to 18 carbon atoms, it being possible for a straight-chain or branched alkyl radical ($C_1$ to $C_6$) to be substituted by an aromatic radical ($C_6$ to $C_{12}$). Examples which may be mentioned are benzyl, phenyl-ethyl and phenyl-propyl. Benzyl is preferred.

The aryl and aralkyl radicals can optionally be substituted. Examples of substituents which may be mentioned are lower alkyl ($C_1$ to about $C_6$), aryl ($C_6$ to $C_{12}$) and halogen, preferably fluorine and chlorine.

The siloxane chain (A) comprises m structural elements of the formula

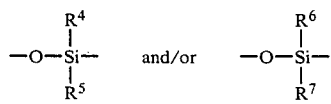

and the terminal group

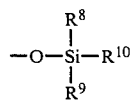

where the substituents $R^4$ to $R^{10}$ have the abovementioned meaning.

The structural elements can be randomly distributed or associated into larger structural regions (blocks). It is also possible for the siloxane chain to comprise only one type of structural element.

An alkylene chain (W) generally represents a divalent, straight-chain or branched hydrocarbon radical having 2 to 10 carbon atoms. Alkylene chains having 2 to 6 carbon atoms are preferred. The following alkylene chains may be mentioned as examples: ethylene, propylene, iso-propylene, 1-methyl-1,3-propylene and 1,2-dimethyl-1,3-propylene.

A divalent, straight-chain or branched aliphatic radical E can denote a hydrocarbon radical having 2 to 24 carbon atoms, preferably 2 to 12 carbon atoms. The following divalent aliphatic radicals may be mentioned as examples: ethylene, propylene, 1,4-tetramethylene, 1,6-hexamethylene or 2,2,4-trimethyl-1,6-hexamethylene, and isomers.

A divalent aromatic radical E can denote a hydrocarbon radical having 6 to 26, preferably 6 to 18, carbon atoms. The following aromatic radicals may be mentioned as examples:

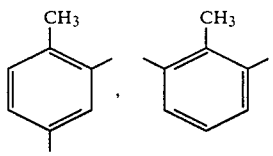

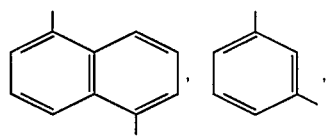

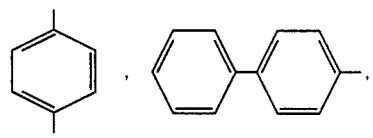

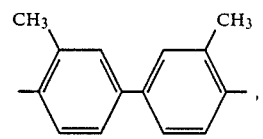

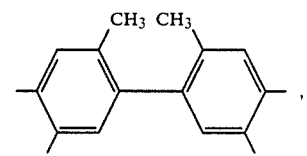

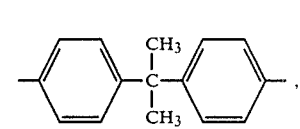

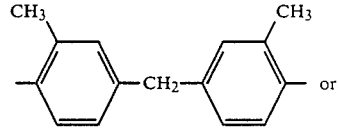

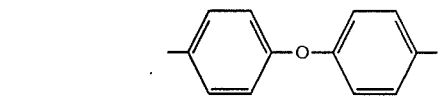

A divalent araliphatic radical E can denote a hydrocarbon radical having a straight-chain or branched aliphatic and an aromatic part having 7 to 20 carbon atoms, the aromatic part preferably containing 6 to 12 carbon atoms and the aliphatic part preferably containing 1 to 8 carbon atoms. The following araliphatic radicals may be mentioned as examples:

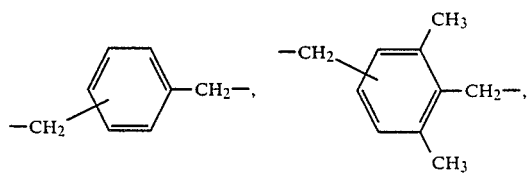

-continued

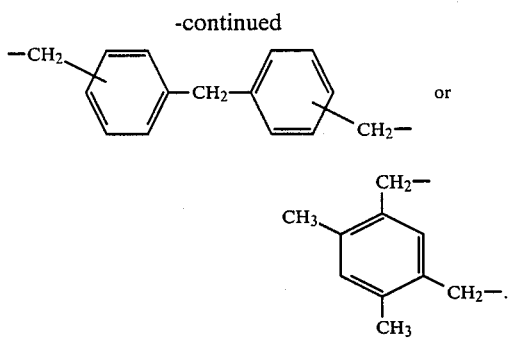

or

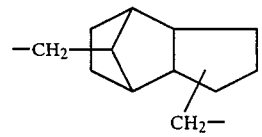

A divalent cycloaliphatic radical E can denote a hydrocarbon radical having 6 to 26, preferably 6 to 14, carbon atoms. The following may be mentioned as examples:

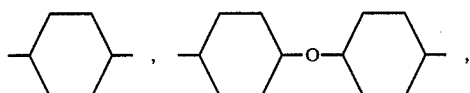

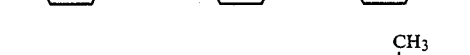

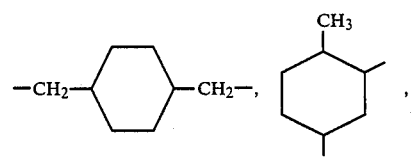

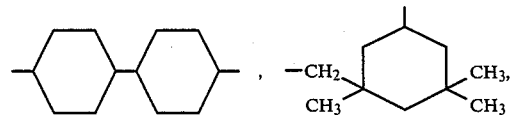

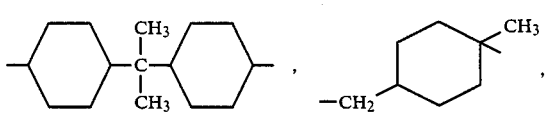

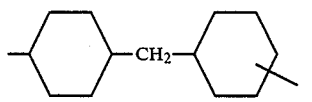

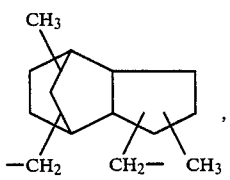

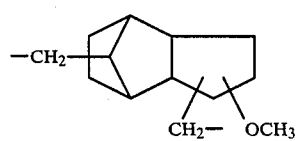

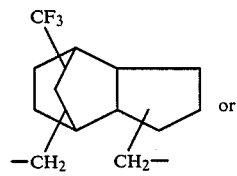

It is also possible for several (preferably 1 to 3) of the aromatic, araliphatic and/or cycloaliphatic radicals mentioned to be connected via optionally substituted methylene groups.

Optionally substituted methylene groups can be, for example, the groups $$-CH_2-, \quad -\underset{\underset{\displaystyle CH_3}{|}}{\overset{\overset{\displaystyle CH_3}{|}}{CH}}-, \quad -\underset{\underset{\displaystyle CH_3}{|}}{\overset{\overset{\displaystyle CH_3}{|}}{C}}-, \quad -\underset{\underset{\displaystyle C_2H_5}{|}}{\overset{\overset{\displaystyle C_2H_5}{|}}{CH}}- \quad \text{or} \quad -\underset{\underset{\displaystyle C_2H_5}{|}}{\overset{\overset{\displaystyle C_2H_5}{|}}{C}}-$$

A divalent hydrocarbon radical G can denote a straight-chain or branched aliphatic hydrocarbon having 3 to 15 carbon atoms, preferably 3 to 10 carbon atoms. The radical G can optionally contain 1 to 3 oxygen bridges, preferably 1 to 2 oxygen bridges. It is also possible for the radical G to be substituted by 1 to 4, preferably 1 or 2, (meth)acrylate radicals. The following radicals may be mentioned as examples:

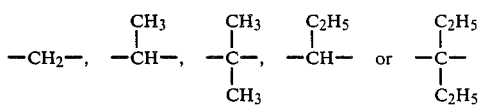

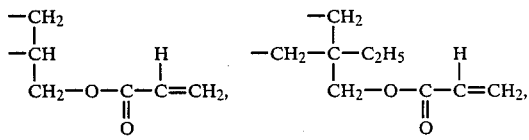

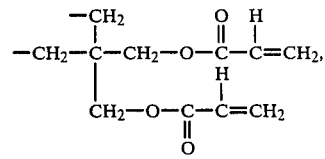

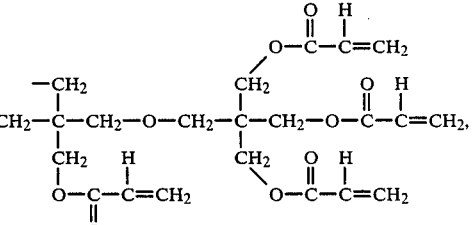

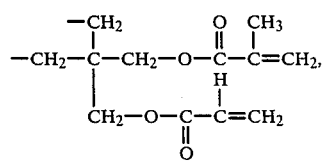

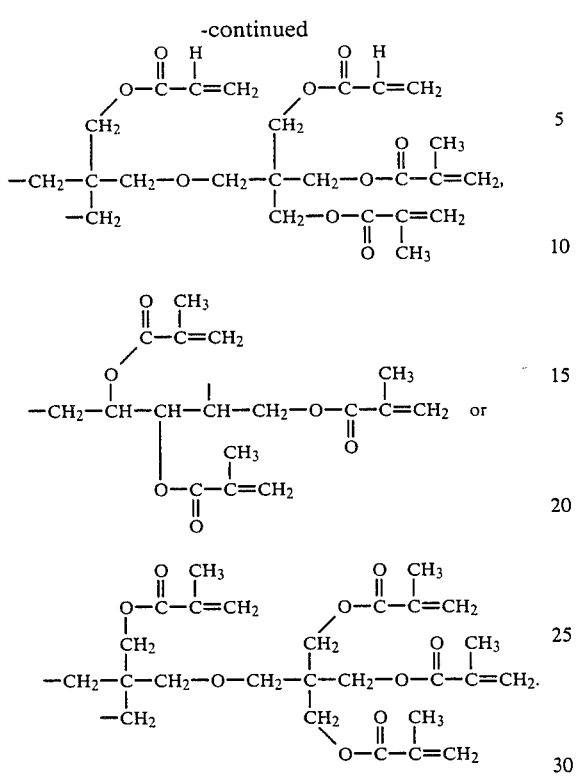

In general, the siloxane chain comprises a total of 0 to 600, preferably 0 to 200, particularly preferably 0 to 50, structural elements (m). In the case where the number of structural elements (m) equals 0 and B represents lower alkyl, the siloxane chain comprises only the terminal group (disiloxane).

For the processes according to the invention, substitution of 0.5 to 100 mol %, particularly 10 to 100 mol %, of all silicon atoms by tricyclo[5.2.1.0$^{2.6}$]-decanyl groups is preferred.

In the context of the present invention, preferred (meth)-acrylates of siloxanes containing tricyclodecane groups are those of the formula

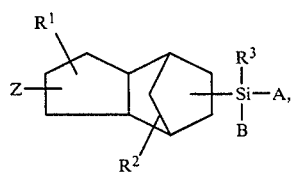

in which

R$^1$ and R$^2$ are idential or different and denote hydrogen, lower alkyl, halogen or trifluoromethyl, R$^3$ denotes lower alkyl, cycloalkyl (C$_5$ to C$_7$), cycloalkyl-alkyl (C$_6$ to C$_{13}$) or optionally substituted aryl (C$_6$ to C$_{12}$) or aralkyl (C$_7$ to C$_{18}$), Z represents the

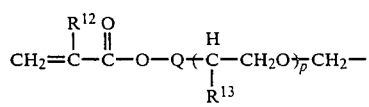

group, in which

R$^{12}$ and R$^{13}$ are identical or different and denote hydrogen or methyl, p represents a number from 0 to 20, and Q represents a single bond or denotes a radical of the formula

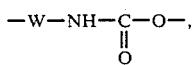

in which

W denotes an alkylene chain having 2 to 10 carbon atoms, or denotes a radical of the formula

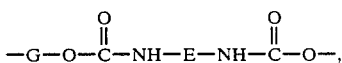

in which

E is a divalent, straight-chain or branched aliphatic radical having 2 to 12 carbon atoms, an aromatic radical having 6 to 18 carbon atoms, or a cycloaliphatic radical having 6 to 14 carbon atoms, it being possible for the aliphatic, aromatic and/or cycloaliphatic radicals to contain 1 or 2 oxygen bridges, and it being possible for several of the aliphatic, aromatic and/or cycloaliphatic radicals to be connected via optionally substituted methylene groups, and G denotes a divalent straight-chain or branched aliphatic hydrocarbon radical, having 3 to 10 carbon atoms, which can optionally contain 1 to 3 oxygen bridges and can optionally be substituted by 1 or 2 additional (meth)-acryloyloxy radicals, A represents a siloxane chain which comprises m stuctural elements of the formula

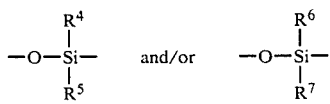

and the terminal group

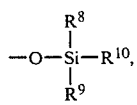

where

R$^4$, R$^5$, R$^6$, R$^7$, R$^8$ and R$^9$ are identical or different and denote lower alkyl, cycloalkyl (C$_5$ to C$_7$), cycloalkyl-alkyl (C$_6$ to C$_{13}$) or optionally substituted aryl (C$_6$ to C$_{12}$) or aralkyl (C$_7$ to C$_{18}$), where the radicals R$^5$, R$^7$ and R$^8$ alternatively represent the

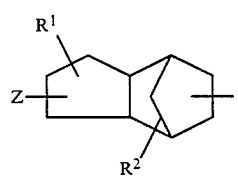

group, in which
R$^1$, R$^2$ and Z have the abovementioned meaning,
R$^{10}$ represents lower alkyl, and
where the total number of structural elements m, independently of one another, represent a number from 0 to 200, and
B can have the same range of meanings as A, it being possible for the radicals R$^4$ to R$^{10}$ in chains A and B to be different, or represents lower alkyl.

In addition, particularly preferred (meth)acrylates of siloxanes containing tricyclodecane groups are those of the formula

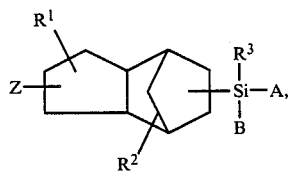

in which
R$^1$ and R$^2$ are identical or different and denote hydrogen or lower alkyl,
R$^3$ denotes lower alkyl, cycloalkyl (C$_5$ to C$_7$), cycloalkyl-alkyl (C$_6$ to C$_{10}$), or optionally substituted aryl (C$_6$ to C$_{11}$) or aralkyl (C$_7$ to C$_{11}$),
Z represents the

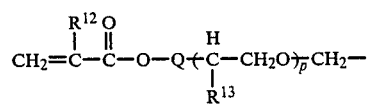

group, in which
R$^{12}$ and R$^{13}$ are identical or different and denote hydrogen or methyl,
p represents a number from 0 to 4, and
Q represents a single bond or denotes a radical of the formula

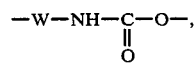

in which
W denotes an alkylene chain having 2 to 6 carbon atoms,
or denotes a radical of the formula

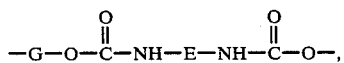

in which
E is a divalent, straight-chain or branched aliphatic radical having 2 to 8 carbon atoms or a cycloaliphatic radical having 6 to 14 carbon atoms, and
G denotes a divalent straight-chain or branched aliphatic hydrocarbon radical, having 3 to 10 carbon atoms, which may optionally contain 1 oxygen bridge and may optionally be substituted by 1 or 2 additional (meth)acryloyloxy radicals,
A represents a siloxane chain which comprises m structural elements of the formula

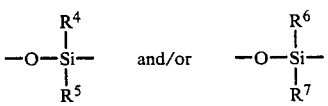

and the terminal group

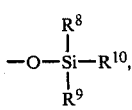

where
R$^4$, R$^5$, R$^6$, R$^7$, R$^8$ and R$^9$ are identical or different and denote lower alkyl, cycloalkyl (C$_5$ to C$_7$), cycloalkyl-alkyl (C$_6$ to C$_{10}$), or optionally substituted aryl (C$_6$ to C$_{11}$) or aralkyl (C$_7$ to C$_{11}$),
where the radicals R$^5$, R$^7$ and R$^8$ alternatively represent the

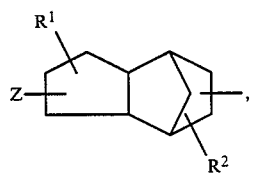

group in which
R$^1$, R$^2$ and Z have the abovementioned meaning,
R$^{10}$ represents lower alkyl, and where the total number of structural elements m, independently of one another, represent a number from 0 to 200, and
B can have the same range of meanings as A, it being possible for the radicals R$^4$ to R$^{10}$ in chains A and B to be different, or represents lower alkyl.

The following (meth)acrylates of siloxanes containing tricyclodecane groups may be mentioned as examples:

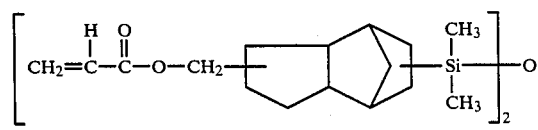

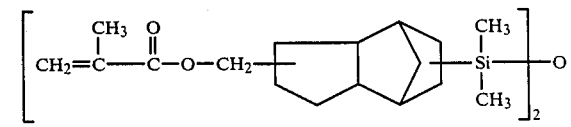

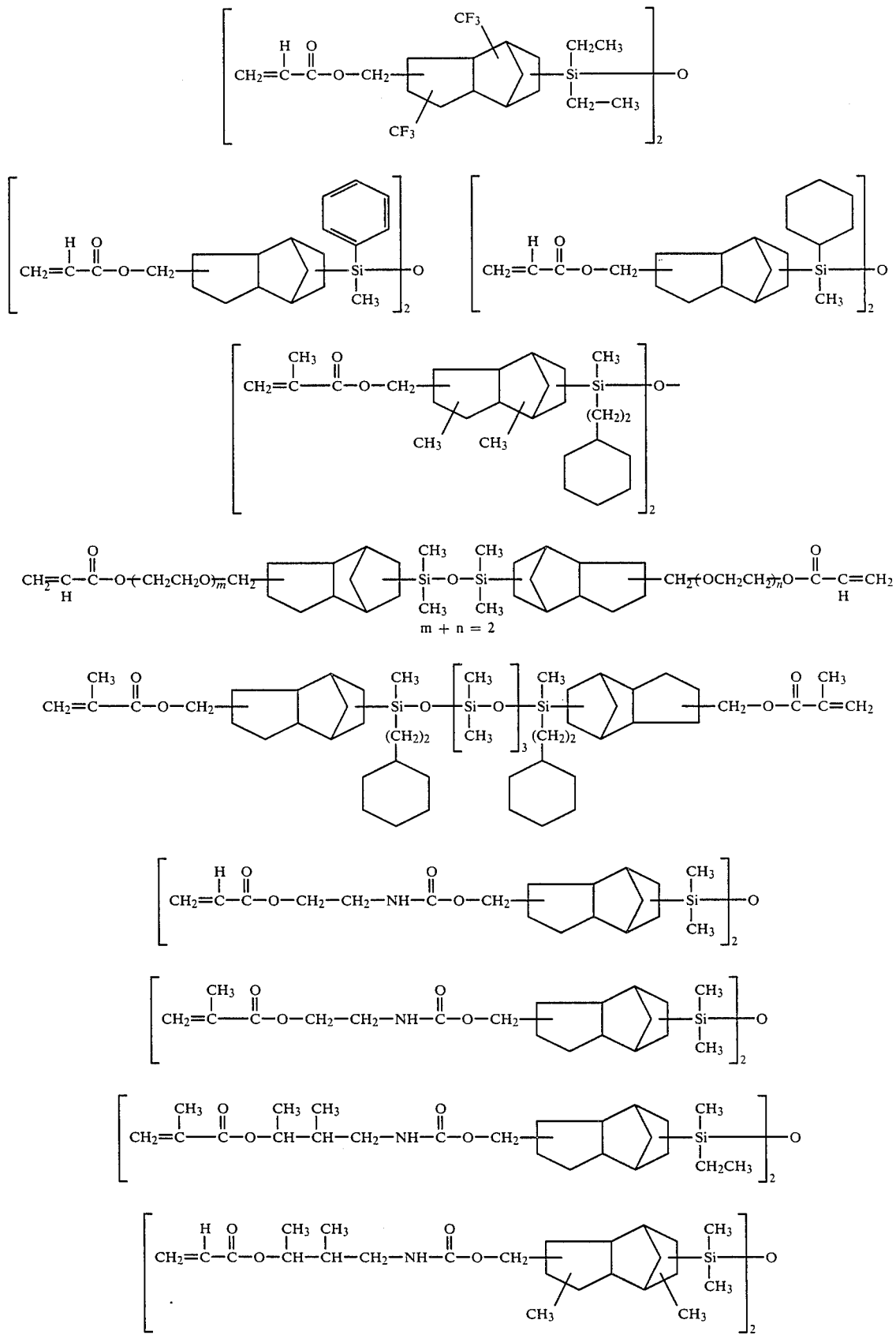

-continued

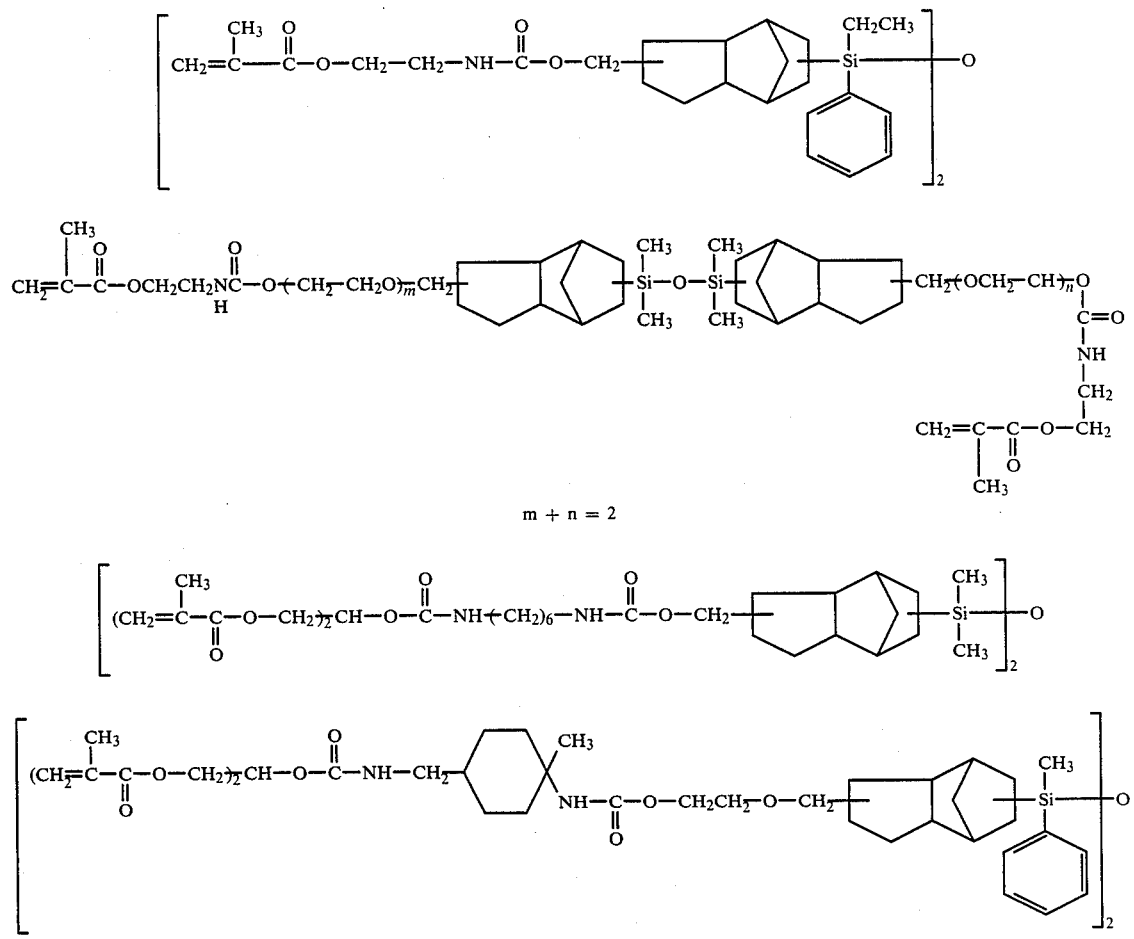

A process has also been found for the preparation of (meth)acrylates of siloxanes containing tricyclodecane groups, of the formula

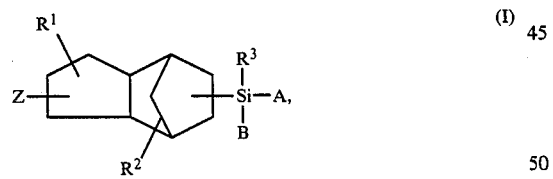

(I)

in which
R¹ and R² are identical or different and denote hydrogen, lower alkyl, halogen or trifluoromethyl,
R³ denotes lower alkyl, cycloalkyl, cycloalkyl-alkyl or optionally substituted aryl or aralkyl,
Z represents the

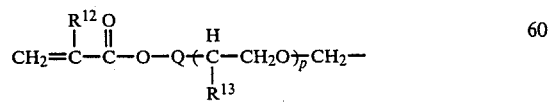

group, in which
R¹² and R¹³ are identical or different and denote hydrogen or methyl,
p represents a number from 0 to 20 and
Q represents a single bond, or denotes a radical of the formula

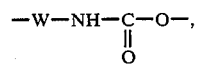

in which
W denotes an alkylene chain,
or denotes a radical of the formula

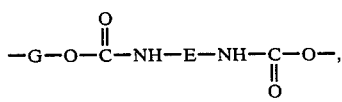

in which
E is a divalent, straight-chain or branched aliphatic radical having 2 to 24 carbon atoms, an aromatic radical having 6 to 26 carbon atoms, an araliphatic radical having 7 to 26 carbon atoms, or a cycloaliphatic radical having 6 to 26 carbon atoms, it being possible for the aliphatic, aromatic, araliphatic and/or cycloaliphatic radicals to contain 1 or 2 oxygen bridges, and it being possible for several of the aliphatic, aromatic, araliphatic and/or cycloaliphatic radicals to be connected via optionally substituted methylene groups, and G denotes a divalent straight-chain or branched aliphatic hydrocarbon radical, having 3 to 15 carbon atoms, which may optionally contain 1 to 3 oxygen bridges and may optionally be substituted by 1 to 4 additional (meth)acryloyloxy radicals, A represents a siloxane chain which comprises m structural elements of the formula

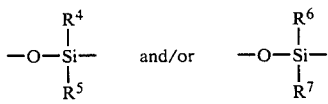

and the terminal group

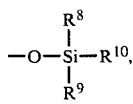

where
$R^4$, $R^5$, $R^6$, $R^7$, $R^8$ and $R^9$ are identical or different and denote lower alkyl, cycloalkyl, cycloalkylalkyl or optionally substituted aryl or aralkyl,
where the radicals $R^5$, $R^7$ and $R^8$ alternatively represent the

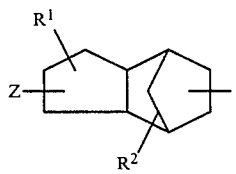

group, in which
$R^1$, $R^2$ and Z have the abovementioned meaning,
$R^{10}$ represents lower alkyl, and where the total number of structural elements m, independently of one another, represent a number from 0 to 600, and B can have the same range of meanings as A, it being possible for the radicals $R^4$ to $R^{10}$ in chains A and B to be different, or represents lower alkyl, which is characterized in that poly[hydroxy(alkyleneoxy)methyl-tricyclo-[5.2.1.0$^{2.6}$]-decanyl]-siloxanes of the formula

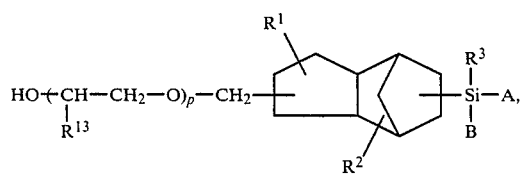 (II)

in which
$R^1$, $R^2$, $R^3$, $R^{13}$, p, A and B have the abovementioned meaning,
in the case of the preparation of compounds in which Q represents a single bond, are esterified using a (meth)acrylic acid derivative of the formula

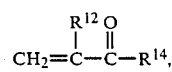 (III)

in which
$R^{12}$ has the abovementioned meaning, and
$R^{14}$ represents hydroxyl, chlorine, methoxy, ethoxy or (meth)acryloyloxy, or in the case of the preparation of compounds in which Q represents a radical of the formula

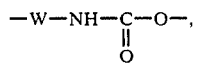

in which
W represents an alkylene chain,
are reacted with an isocyanate of the formula

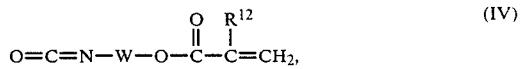 (IV)

in which
$R^{12}$ and W have the abovementioned meaning, in an inert solvent, or, in the case of the preparation of compounds in which Q represents a radical of the formula

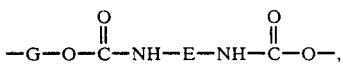

in which
E is a divalent, straight-chain or branched aliphatic radical having 2 to 24 carbon atoms, an aromatic radical having 6 to 26 carbon atoms, an araliphatic radical having 7 to 26 carbon atoms or a cycloaliphatic radical having 6 to 26 carbon atoms, it being possible for the aliphatic, aromatic, araliphatic and/or cycloaliphatic radicals to contain 1 or 2 oxygen bridges, and it being possible for several of the aliphatic, aromatic, araliphatic and/or cycloaliphatic radicals to be connected via optionally substituted methylene groups, and
G denotes a divalent straight-chain or branched aliphatic hydrocarbon radical, having 3 to 15 carbon atoms, which may optionally contain 1 to 3 oxygen bridges and may optionally be substituted by 1 to 4 additional (meth)-acryloyloxy radicals, are reacted with the product of the addition reaction of 1 mole of a diisocyanate of the formula

 (V), in which
E has the abovementioned meaning,
and 1 mole of a hydroxyalkyl (meth)-acrylate of the formula

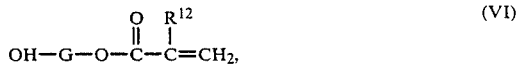 (VI)

in which
G and $R^{12}$ have the abovementioned meaning,
where a stoichiometric equivalence exists between the NCO groups of the adduct of V and VI and the OH groups of II, in an inert solvent.

The process according to the invention can be illustrated by the following equation:

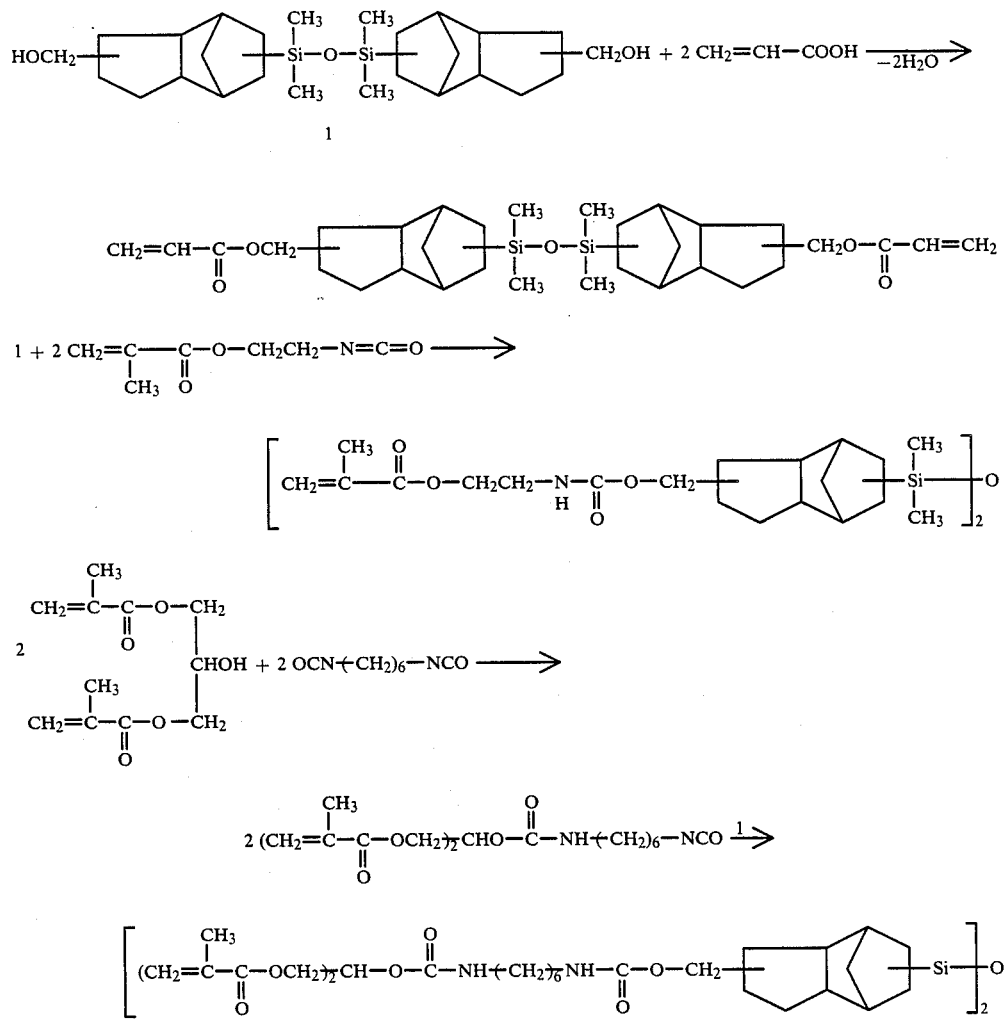

Poly[hydroxy(alkyleneoxy)methyl-tricyclo-[5.2.1.0$^{2.6}$]decanyl]-siloxanes of the formula

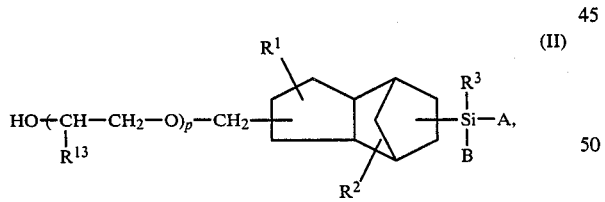

(II)

in which
R$^1$ and R$^2$ are identical or different and denote hydrogen, lower alkyl, halogen or trifluoromethyl,
R$^3$ denotes lower alkyl, cycloalkyl, cycloalkyl-alkyl, or optionally substituted aryl or aralkyl,
R$^{13}$ denotes hydrogen or methyl,
P represents an integer from 0 to 20,
A represents a siloxane chain which comprises m structural elements of the formula $$-O-\underset{\underset{R^5}{|}}{\overset{\overset{R^4}{|}}{Si}}- \quad \text{and/or} \quad -O-\underset{\underset{R^7}{|}}{\overset{\overset{R^6}{|}}{Si}}-$$

and the terminal group $$-O-\underset{\underset{R^9}{|}}{\overset{\overset{R^8}{|}}{Si}}-R^{10},$$

where
R$^4$, R$^5$, R$^6$, R$^7$, R$^8$ and R$^9$ are identical or different and denote lower alkyl, cycloalkyl, cycloalkyl-alkyl, or optionally substituted aryl or aralkyl,
where the radicals R$^5$, R$^7$ and R$^8$ alternatively represent the

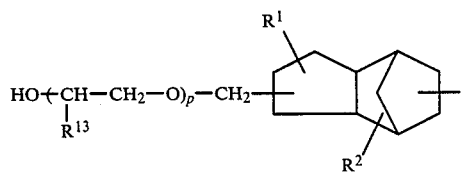

group, in which
R$^1$, R$^2$, R$^{13}$ and p have the abovementioned meaning,
R$^{10}$ represents lower alkyl, and where the number of structural elements m, independently of one another, in each case represents a number from 0 to 600, and B can have the same range of meanings as A, it being possible for the radicals $R^4$ to $R^{10}$ in chains A and B to be different, or represents lower alkyl, can be prepared by initially homocondensing a tricyclo-[5.2.1.0²·⁶]-decenyl-silane of the formula

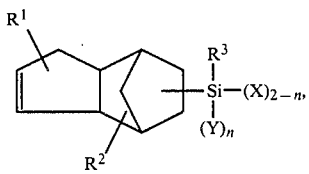
(VII)

in which $R^1$, $R^2$ and $R^3$ have the abovementioned meaning,

X represents a hydrolysable radical,

Y represents lower alkyl, and n represents the number 0 or 1, in the presence of water and a condensation catalyst, or cocondensing the silane (VII) with diorgano-silanes of the formulae

(VIII)

and/or

(IX)

and subsequently, in the case where n equals 0, reacting with triorgano-silanes of the formula

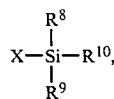
(X)

where X, $R^4$, $R^6$, $R^9$ and $R^{10}$ have the abovementioned meaning, and where $R^{5'}$, $R^{7'}$ and $R^{8'}$ are identical or different and denote lower alkyl, cycloalkyl, cycloalkylalkyl, or optionally substituted aryl or aralkyl, or alternatively represent the

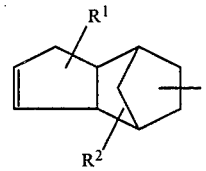

group, in which $R^1$ and $R^2$ have the abovementioned meaning, where the silanes VII to silanes X molar ratio after the homocondensation of the silanes VII or after the cocondensation of the silanes VII with the silanes VIII and/or IX is greater than or equal to 0.5 and where m moles of the silanes VIII and/or IX, relative to 1 mole of the silane of the formula VII, are employed for the cocondensation, where m has the abovementioned meaning, and then reacting the resultant poly(tricyclo[5.2.1.0²·⁶]-decenyl)-siloxane with carbon monoxide and hydrogen (in the approximate ratio 1:1) in the presence of a hydroformylation catalyst, reducing the resultant formyl derivative, in a further stage, to the hydroxymethyl derivative, and reacting the resultant hydroxymethyl derivative, if appropriate (for p>0), with p moles, relative to 1 mole of hydroxymethyl groups, of an alkylene oxide of the formula

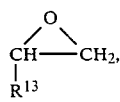
(XI)

where $R^{13}$ and p have the abovementioned meaning, in the presence of a basic catalyst.

The preparation process can be illustrated by the following equation:

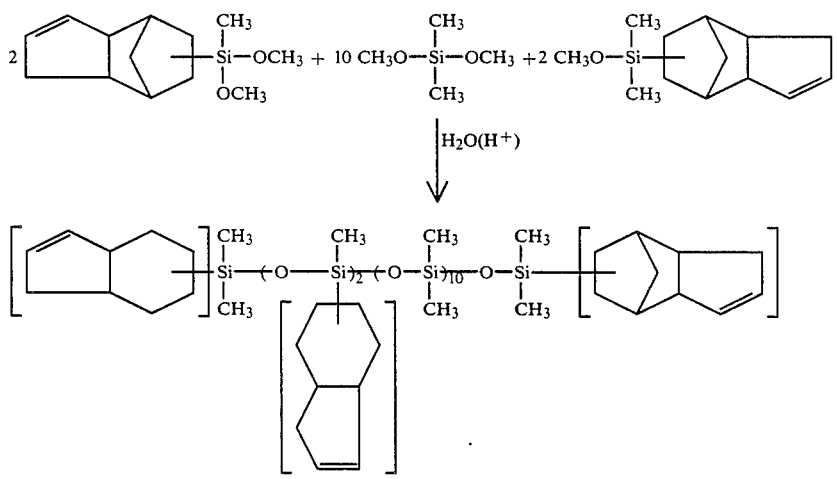

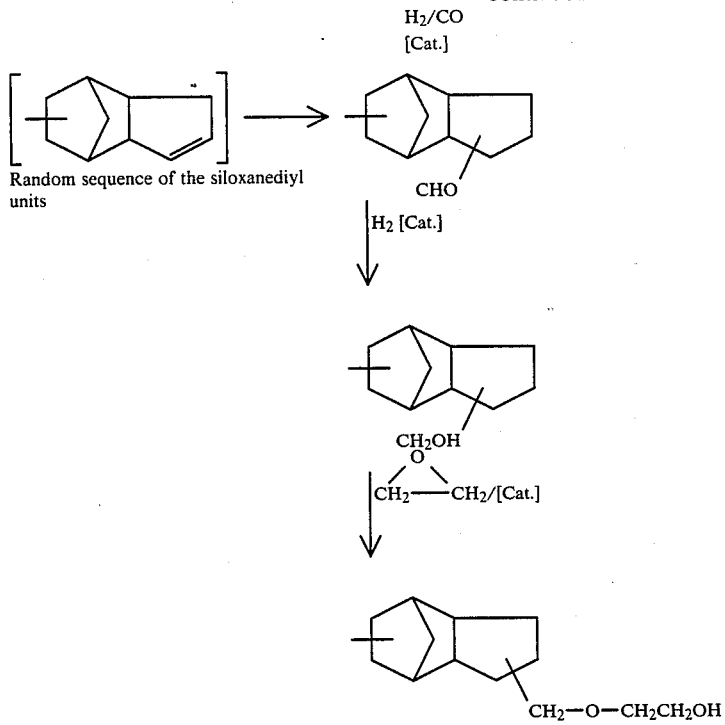

Tricyclo-[5.2.1.0$^{2.6}$]-decenyl-silanes (VII) are known per se (Chem. Abstr. 94, 15799 and 85, 143 184, 77, 88573). The tricyclo-[5.2.1.0$^{5.6}$]-decenyl-silanes contain a hydrolyzable radical which is cleaved off during the condensation. Hydrolyzable radicals which may be mentioned as examples are halogens (chlorine, bromine and iodine, preferably chlorine), alkoxy ($C_1$ to $C_6$, preferably methoxy and ethoxy), acyloxy and dialkylamino (alkyl, preferably methyl and ethyl).

The tricyclo-[5.2.1.0$^{2.6}$]-decenyl-silanes can be prepared, for example, by reacting 3(4),8-tricyclo-[5.2.1.0$^{2.6}$]-decadiene derivatives with appropriate hydrogensilanes in the presence of hydrosilylation catalysts, for example $H_2PtCl_6$.

Diorgano-silanes (VII and IX) are commercially available or can be prepared, in the case where R$^{5'}$ and R$^{7'}$ represent a tricyclo[5.2.1.0$^{2.6}$]-decenyl radical, by reacting 3(4),8-tricyclo[5.2.1.0$^{2.6}$]decadiene derivatives with hydrogensilanes, for example methyldichlorosilane. The following diorganosilanes may be mentioned as examples:

dimethyldichlorosilane, dimethoxydimethylsilane, ethylmethyldichlorosilane, methylphenyldimethoxysilane, diphenyldiethoxysilane, (2-cyclohexylethyl-1-yl)-ethyl-dichlorosilane, dibutyl-dimethoxysilane, di-n-propyldi-chlorosilane, methyl-tricyclo[5.2.10$^{2.6}$]decenyldichlorosilane and methyl-tricyclo[5.2.1.0$^{2.6}$]decenyldimethoxysilane.

Triorganosilanes (X) are commercially available or, in the case where R$^{8'}$ represents a tricyclo[5.2.1.0$^{2.6}$]-decenyl radical, can be prepared in an analogous fashion to that described for VIII and IX.

The following triorganosilanes may be mentioned as examples: trimethylchlorosilane, trimethylmethoxysilane, diethylpropyl-ethoxysilane, diphenyl-methyl-methoxysilane, tricyclo[5.2.1.0$^{2.6}$]decenyl-dimethyl-chlorosilane and tricyclo[5.2.1.0$^{2.6}$]decanyldimethylmethoxysilane.

Condensation catalysts (W. Noll, Chemie und Technologie der Silicone [The Chemistry and Technology of the Silicones], Verlag Chemie (1968)) for the homocondensation/cocondensation are, for example, hydrohalic acids, sulphuric acid, alkali metal salts, alkali metal and alkaline-earth metal hydroxides, carbonates and oxides, trifluoroacetic acid, perfluorobutanesulphonic acid and acetic acid.

The homocondensation/cocondensation is generally carried out at atmospheric pressure and at temperatures from $-20°$ to $+80°$ C. with an excess of water in the presence of the condensation catalyst, which, for example in the case of halogenosilanes, is formed in situ during the hydrolysis. The homocondensation or cocondensation can also be carried out in the presence of solvents which are water-miscible or water-immiscible. The following solvents may be mentioned as examples: toluene, dichloromethane, chloroform, diethyl ether, tetrahydrofuran, methyl ethyl ketone, acetone, hexane, ethanol, isopropanol, methanol and ethyl acetate.

After the homocondensation of tricyclo[5.2.1.0$^{2.6}$]-decenylsilanes VIII, in the case where n equals 0, and after the cocondensation with diorganosilanes VIII and/or IX, the aqueous phase is separated off and the reaction mixture is equilibrated in an inert solvent with acidic or basic catalysts of the abovementioned type, preferably perfluorobutanesulphonic acid. During this equilibration, the mixtures of cyclic and linear polysiloxanes produced initially are converted into mixtures of linear polysiloxanes having relatively high uniformity and a relatively high molecular weight. The course of the reaction can be followed, for example, by measuring the viscosity.

After the equilibration step, mainly polysiloxanes having silanol terminal groups are produced. These polysiloxanes are subsequently reacted with triorganosilanes X in the presence of condensation catalysts in order to convert the silanol terminal groups present into triorganosiloxy terminal groups.

However, it is also possible to employ a triorganosilane X directly in the homocondensation/cocondensation, it acting as chain terminator and being introduced into the polysiloxane as a triorganosiloxy terminal group.

In the case where n in the formula VII equals 1, i.e. the tricyclo[5.2.1.0$^{2,6}$]decenylsilane VII only has one hydrolyzable group, the reaction with triorganosilanes X is superfluous since, in the homocondensation, the corresponding disiloxane is produced from a silane VII of this type in which n equals 1, and, in the case of the cocondensation with diorganosilanes of the formula VI and/or IX, polysiloxanes which already contain the silyl radical of the silane VII as a terminal group are produced.

The further reaction of the poly-(tricyclo-[5.2.1.0$^{2,6}$]decenyl) compounds to form the formyl derivatives is generally carried out with carbon monoxide and hydrogen in the presence of a hydroformylation catalyst. Carbon monoxide and hydrogen are generally employed in the approximate ratio 1 to 1.

The hydroformylation catalysts used are generally rhodium catalysts (Houben-Weyl, Methoden der organischen Chemie [Methods of Organic Chemistry], vol. E3, pp. 180 ff. (1983)). The so-called Wilkinson complex or bis-(dicarbonylchlororhodium), for example, is preferred. A heterogeneous catalyst which, for example, contains 5% of rhodium on aluminum oxide is particularly preferred.

In general, $10^{-3}$ to $10^{-7}$ mole, preferably $10^{-3}$ to $10^{-5}$ mole, of rhodium, relative to one mole of tricyclo-[5.2.1.0$^{2,6}$]decenyl groups, is employed.

The hydroformylation is generally carried out in the pressure range 30 to 250 bar of carbon monoxide/hydrogen and in the temperature range 50° to 180° C., preferably 70° to 150° C.

The hydroformylation can preferably be carried out in the presence of a solvent. Solvents which may be mentioned as examples are methylcyclohexane, toluene and xylene.

The resultant formyl compound according to the invention can be isolated in a fashion known per se, for example by removing the solvent and purifying over an adsorbent.

The hydrogenation of the formyl compounds to form the alcohol is carried out in the presence of a hydrogenation catalyst at a hydrogen pressure of 5 to 250 bar, preferably 50 to 200 bar, and in the temperature range 20° to 180° C., preferably 60°–150° C., in inert solvents, for example saturated hydrocarbons or aliphatic alcohols. Saturated hydrocarbons which may be mentioned as examples are: cyclohexane, n-hexane, n-heptane and methylcyclohexane. Suitable alcohols are lower alcohols, for example methanol, ethanol, isopropanol, n-propanol and n-butanol. Aliphatic alcohols are preferred as solvent.

The hydrogenation catalyst is, for example, a transition metal, which is employed in the form of its salts or complexes, or in the form of a supported catalyst. The following hydrogenation catalysts may be mentioned as examples: tris(triphenylphosphine)chloro-rhodium, Raney nickel, bis(dicarbonylchlororhodium) and 5% rhodium on aluminum oxide.

Activators can be added, if appropriate, to accelerate the hydrogenation. Suitable activators are, for example: sodium hydroxide, triethylamine, tri-n-butylamine, pyridine and hexachloroplatinic acid. The catalyst is employed in an amount from 1 to $10^{-6}$ mole, preferably $10^{-1}$ to $10^{-4}$ mole, of metal, relative to 1 mole of formyl groups. The activator is employed in an amount from $10^{-1}$ to $10^{-6}$ mole, relative to 1 mole of metal.

The hydrogenation is followed by IR spectroscopy and is continued until quantitative reduction of all formyl groups has been achieved.

When the hydrogenation is complete, the poly-(hydroxymethyl-tricyclo[5.2.1.0$^{2,6}$]decanyl)siloxane produced can be freed of catalyst and impurities by filtration and/or using adsorbents such as Celite ®, silica gel or aluminum oxide, and can be isolated by removing the solvent in vacuo. The siloxane derivatives are obtained as colorless highly-viscous to waxy substances. If appropriate, purification can also be effected by vacuum distillation if the products are, for example, disiloxanes.

This poly(hydroxymethyl-tricyclo[5.2.1.0$^{2,6}$]-decanyl)siloxane can be reacted with 1–20 moles (relative to 1 mole of hydroxymethyl groups) of an alkylene oxide, for example oxirane or methyloxirane, at temperatures from 70° to 150° C., preferably 90° to 120° C., if appropriate in the presence of basic catalysts, to form compounds of the formula II, the alkylene oxide expediently being metered in to the extent of its consumption.

The basic catalysts used are preferably alkali metal or alkaline-earth metal alcoholates, which can also be prepared in situ.

A further process for the preparation of α,ω-bis-[hydroxy(alkyleneoxy)methyl-tricyclo[5.2.1.0$^{2,6}$]-decanyl]-siloxanes of the formula

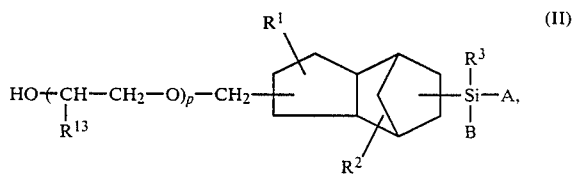

in which
R$^1$ and R$^2$ are identical or different and denote hydrogen, lower alkyl, halogen or trifluoromethyl,
R$^3$ denotes lower alkyl, cycloalkyl, cycloalkyl-alkyl, or optionally substituted aryl or aralkyl,
R$^{13}$ denotes hydrogen or methyl,
P represents an integer from 0 to 20,
A represents a siloxane chain which comprises m structural elements of the formula

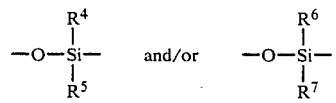

and the terminal group

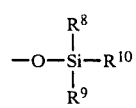

where
R$^4$, R$^5$, R$^6$, R$^7$ and R$^8$ are identical or different and denote lower alkyl, cycloalkyl (C$_5$ to C$_7$), cycloalkyl-alkyl (C$_6$ to C$_{10}$), or optionally substituted aryl (C$_6$ to C$_{11}$) or aralkyl (C$_7$ to C$_{11}$), $R^8$ represents the

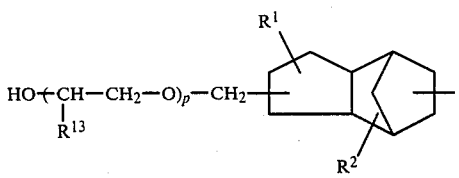

group, in which
$R^1$, $R^2$, $R^{13}$ and p have the abovementioned meaning,
$R^{10}$ represents lower alkyl, and where the total number of structural elements m, independently of one another, represent a number from 0 to 600, and
B represents lower alkyl,
is characterized in that, in a first stage, an α,ω-bis-hydrogensiloxane of the formula

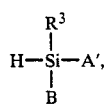 (XII)

in which
A' represents a siloxane chain which comprises m structural elements of the formula

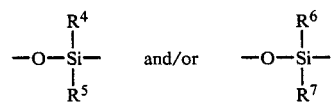

and the terminal group

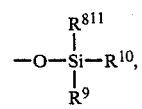

where
$R^4$, $R^5$, $R^6$, $R^7$, $R^9$ and $R^{10}$ have the abovementioned meaning, and
$R^{8''}$ represents hydrogen, where the total number of structural elements m, independently, represents a number from 0 to 600, and
B and $R^3$ have the abovementioned meaning,
is reacted with a tricyclo-[5.2.1.0$^{2.6}$]-decadiene derivative of the formula

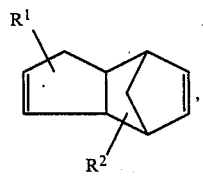 (XIII)

in which
$R^1$ and $R^2$ have the abovementioned meaning,
in the presence of noble-metal catalysts, or in that bis-(tricyclo[5.2.1.0$^{2.6}$]decenyl)-disiloxanes of the formula

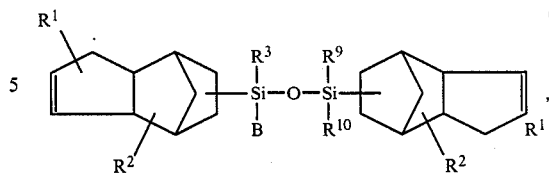 (XIV)

in which
$R^1$, $R^2$, $R^3$, $R^9$, $R^{10}$ and B have the abovementioned meaning,
are equilibrated, in the presence of acids or bases, with a cyclosiloxane of the formula

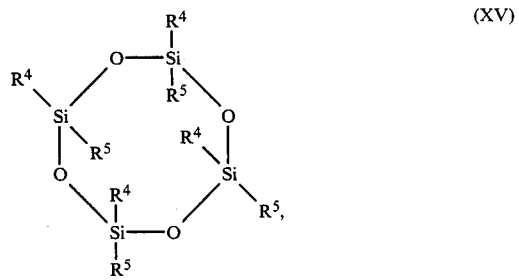 (XV)

in which
$R^4$ and $R^5$ have the abovementioned meaning,
and/or with a cyclo-siloxane of the formula

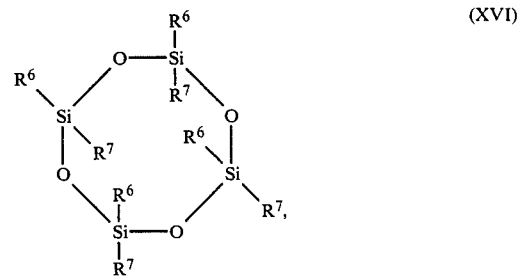 (XVI)

in which
$R^6$ and $R^7$ have the abovementioned meaning, and the α,ω-bis-(tricyclo-[5.2.1.0$^{2.6}$]-decenyl)-siloxane obtained by the variants is then, in a following stage, reacted with carbon monoxide and hydrogen in the approximate ratio 1:1 in the presence of a hydroformylation catalyst,
the formyl derivative obtained is reduced, in a further stage, to the corresponding hydroxymethyl derivative, and the hydroxymethyl derivative obtained is, if appropriate (for p>0), reacted with p moles (relative to 1 mole of hydroxymethyl groups) of an alkylene oxide of the formula

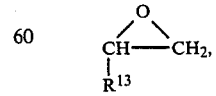

where
$R^{13}$ and p have the abovementioned meaning,
in the presence of a basic catalyst.

The preparation process may be illustrated by the following equation.

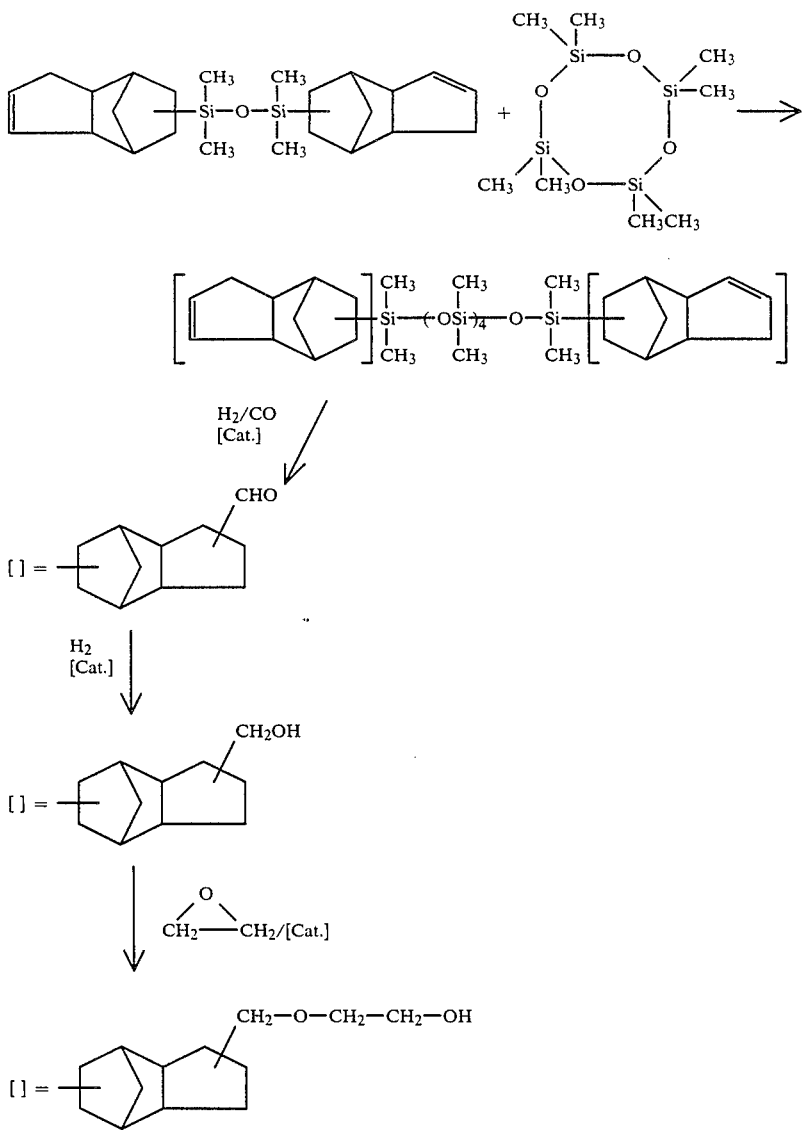

The first stage of this process can be carried out in two variants:

according to the first variant, α,ω-bishydrogensiloxanes (XII) are reacted with a tricyclo-[5.2.1.0²·⁶]-decadiene derivative (XIII).

α,ω-Bishydrogensiloxanes (XII) are commercially available and can be prepared, for example, by equilibrating dihydrogentetraorganodisiloxanes with cyclotrisiloxanes.

The following α,ω-bishydrogensiloxanes (XII) may be mentioned as examples:

H—Si(CH₃)₂—O—Si(CH₃)₂—H,

H—Si(CH₃)₂—OSi(CH₃)₂—OSi(CH₃)₂—H

H—(CH₃)₂Si[—O—Si(CH₃)₂]₁₀—OSi(CH₃)₂—H

HSi(CH₃)₂[—OSi(CH₃)₂]₁₅₀—O—Si(CH₃)₂H

-continued

Tricyclo-[5.2.1.0²·⁶]-decadiene derivatives (XIII) are commercially available and can be prepared, for example, by Diels-Alder reaction of appropriate cyclopentadiene derivatives (Houben-Weyl, Methoden der organischen Chemie [Methods of Organic Chemistry], vol. V/1b, pp. 438–447 (1972)).

The following tricyclo-[5.2.1.0²·⁶]decadiene derivatives may be mentioned as examples:

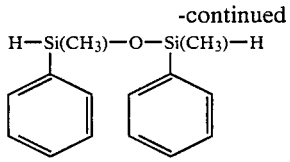

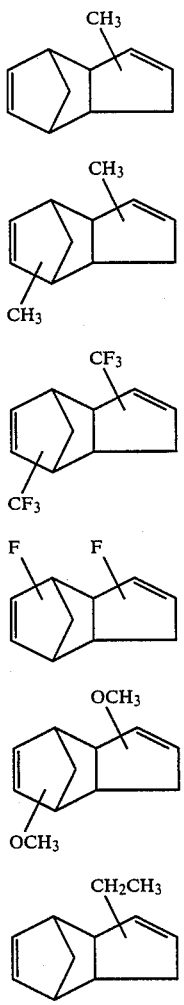

The reaction of α,ω-bishydrogensiloxanes with tricyclo-[5.2.1.0²·⁶]-decadiene derivatives (hydrosilylation) is carried out in the presence of hydrosilylation catalysts. Platinum compounds, such as, for example, hexachloroplatinic acid in isopropanol, the Lamoreaux catalyst (U.S. Pat. No. 3,220,972) or the Karstedt catalyst (U.S. Pat. No. 3,775,452), are preferably used. It is also possible to carry out the hydrosilylation using a supported platinum catalyst, for example platinum on activated charcoal.

The hydrosilylation catalyst is generally employed in an amount from $10^{-7}$ to $10^{-3}$ mole of platinum, preferably $10^{-6}$ to $10^{-3}$ mole of platinum, relative to one mole of SiH groups of the α,ω-bishydrogensiloxane.

The hydrosilylation is generally carried out in the temperature range 20° to 180° C., preferably in the range 50° to 150° C.

In general, the hydrosilylation is carried out at atmospheric pressure. However, it is also possible to carry out the reaction at increased pressure (for example in the pressure range 1.5 to 10 bar).

In general, the hydrosilylation is carried out with exclusion of moisture.

It is possible to carry out the hydrosilylation with or without solvent.

Solvents which may be mentioned are those which are inert under the reaction conditions. Those which may be mentioned as examples are toluene, chlorobenzene, xylene, octahydronaphthalene and ethylene glycol dimethyl ether.

In general, 1.0 to 2.2 moles of the tricyclo-[5.2.1.0²·⁶]decadiene derivative are employed per mole of SiH groups in the α,β-bishydrogensiloxane.

The hydrosilylation reaction can be followed by IR spectroscopy. The end of the reaction can be determined, for example, from the fact that absorption by the SiH group can no longer be observed at about 2,100 cm⁻¹.

In the hydrosilylation, α,ω-bis(tricyclo-[5.2.1.0²·⁶]-decenyl)-siloxanes are obtained. Before the further reaction, it may be expedient to purify the reaction product of this reaction stage. Low-boiling siloxanes, preferably disiloxanes, having tricyclo[5,2,1.0²·⁶]decenyl substituents can be purified by vacuum distillation. In this procedure, it can be expedient to add a polymerization inhibitor, in an amount from 100 to 1,000 ppm, relative to the reactants, before the distillation. Polymerization inhibitors which may be mentioned as examples are 2,6-di-tert-butyl-4-methyl-phenol and hydroquinone monomethyl ether. In general, the polymerization inhibitor is added in an amount from 0.01 to 1% by weight, relative to the reactants. α,ω-Bis(tricyclo[5.2.1.0²·⁶]decenyl)siloxanes having, for example, more than two siloxanediyl groups are freed of catalyst by adsorbents, such as activated charcoal, aluminum oxide or silica gel, Celite etc., and subseqeuently from volatile components by vacuum treatment.

Under the hydrosilylation conditions specified in the context of the process according to the invention, the SiH group is preferably added in the 8 - or 9-position of the 3(4),8-tricyclo[5.2.1.0²·⁶]-decadiene derivatives.

According to the second variant, bis(tricyclo[5.2.1.0²·⁶]-decenyl)-disiloxanes (XIV) are reacted with cyclosiloxanes (XV) and/or (XVI).

Bis-tricyclo-[5.2.1.0²·⁶]-decenyl)-disiloxanes are known per se (Chem. Abst. 85, 143 184) and can be prepared, for example, by reacting tricycle[5.2.1.0²·⁶]-decadiene derivatives with dihydrogentetraorganodisiloxanes.

The following bis-(tricyclo[5.2.1.0²·⁶]-decenyl)-disiloxanes may be mentioned as examples:

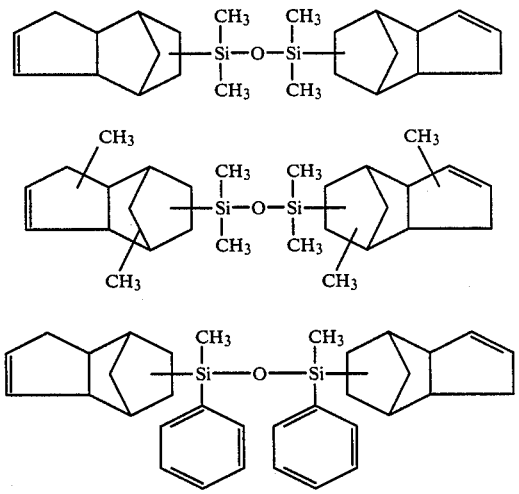

Cyclo-siloxanes (XV) and (XVI) are commercially available and can be obtained, for example, by condensing diorganodihalogenosilanes (Preparative Methods in Polymer Chemistry, Wiley (1969), p. 384 or W. Noll, Chemie and Technologie der Silicone [the Chemistry and Technology of the Silicones], Verlag Chemie (1968)).

The following cyclo-siloxanes may be mentioned as examples: hexamethylcyclotrisiloxane, octamethylcyclotetrasiloxane, tetramethyltetraethylcyclotetrasiloxane and tetramethyltetraphenylcyclotetrasiloxane.

The equilibration is generally carried out in the presence of an acid or base. The acids employed are preferably strong acids having a $p_k$ value of less than 2. The following acids may be mentioned as examples: sulphuric acid, trifluoracetic acid, trifluoromethanesulphonic acid and perfluorobutanesulphonic acid.

The acid is generally employed in an amount from $10^{-3}$ to 5 mol %, preferably $10^{-2}$ to 1.0 mol %, of the reactants.

The bases employed are alkali (alkaline-earth) metal hydroxides, tetraalkylammonium hyroxides, alkali (alkaline-earth) metal oxides or alkali (alkaline-earth) metal carbonates in an amount from $10^{-3}$ to 2 mol % of the reactants.

The equilibration is generally carried out in the temperature range 20° to 120° C., preferably 20° to 80° C.

In general, the equilibration is carried out at atmospheric pressure. However, it is also possible to carry out the equilibration at superatmospheric pressure or subatmospheric pressure (for example in the pressure range $10^{-2}$ to 100 bar.

The equilibration can be carried out with or without solvent. Solvents for this process stage are inert solvents which do not change under the reaction conditions. Examples which may be mentioned are chloroform, toluene, chlorobenzene and hexane.

The course of the reaction can be followed by measuring the viscosity. Equilibrium is reached when a change in viscosity is no longer observed.

The number m of different structural elements in the polysiloxane can be fixed by the molar ratio employed of the cyclo-siloxanes of the formula (XV) and/or (XVI), relative to the bis(tricyclo[5.2.1.0$^{2.6}$]decenyl)-disiloxane (XIV).

When the reaction is complete, the equilibration catalyst is neutralized and/or extracted; volatile components in the reaction mixture can be removed by distillation in vacuo at about 200° C.

The α,ω-bis-tricyclo[5.2.1.0$^{2.6}$]-decenyl)-siloxane obtained by both variants can generally be employed in the further reaction stages after the abovementioned purification processes.

The hydroformylation to form formyl derivatives, the hydrogenation thereof to form the corresponding hydroxymethyl derivatives, and the reaction with alkylene oxides can be carried out the fashion described above.

A further process for the preparation of poly-[hydroxy(alkyleneoxy)methyltricyclo-[5.2.1.0$^{2.6}$]-decanyl]-siloxanes of the formula

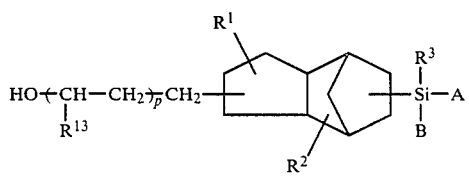

in which
  $R^1$ and $R^2$ are identical or different and denote hydrogen, lower alkyl, halogen or trifluoromethyl,
  $R^3$ denotes lower alkyl, cycloalkyl, cycloalkyl-alkyl, or optionally substituted aryl or aralkyl,
  $R^{13}$ denotes hydrogen or methyl,
  P represents an integer from 0 to 20,
  A represents a siloxane chain which comprises m structural elements of the formula

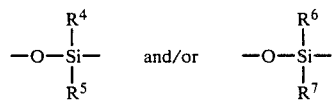

and the terminal group

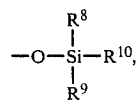

where
    $R^4$, $R^5$, $R^6$, $R^7$, $R^8$ and $R^9$ are identical or different and denote lower alkyl, cycloalkyl, cycloalkylalkyl, or optionally substituted aryl or aralkyl,
  where the radicals $R^5$ and/or $R^7$ alternatively represent the

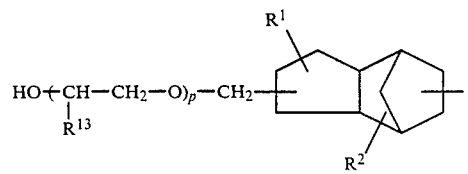

group, in which
    $R^1$, $R^2$, $R^{13}$ and p have the abovementioned meaning,
    $R^{10}$ represents lower alkyl, and where the total number of structural elements m, independently of one another, represent a number from 0 to 600, and
  B can have the same range of meanings as A, where the radicals $R^4$ to $R^{10}$ in the chains A and B can be different,
is characterized in that, in a first stage, a polyhydrogensiloxane of the formula

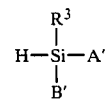 (XVII)

in which
  A' represents a siloxane chain which comprises m structural elements of the formula

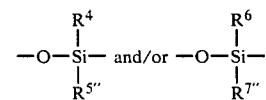

and the terminal group

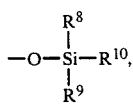

where
R$^{5''}$ and R$^{7''}$ are identical or different and denote hydrogen, lower alkyl, cycloalkyl, cycloalkylalkyl, or optionally substituted aryl or aralkyl, where at least one of the radicals represents hydrogen, m, R$^4$, R$^6$, R$^8$, R$^9$ and R$^{10}$ have the abovementioned meaning, and B' can have the same range of meanings as A', it being possible for the radicals R$^4$, R$^{5''}$, R$^6$, R$^{7''}$, R$^8$, R$^9$ and R$^{10}$ in the chains A' and B' to be different, is reacted with a tricyclo-[5.2.1.0$^{2.6}$]-decadiene derivative of the formula

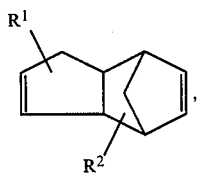 (XVIII)

in which
R$^1$ and R$^2$ have the abovementioned meaning,
in the presence of noble-metal catalysts, and the poly(-tricyclo-[5.2.1.0$^{2.6}$]decenyl)-siloxane obtained is then reacted with carbon monixide and water in the approximate ratio 1:1 in the presence of a hydroformylation catalyst, the formyl derivative obtained is reduced, in a further stage, to the hydroxymethyl derivative, and, if appropriate (for p>0), the hydroxymethyl derivative obtained is reacted with p moles (relative to 1 moles of hydroxymethyl groups) of an alkylene oxide of the formula

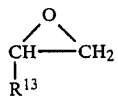

where R$^{13}$ and p have the abovementioned meaning, in the presence of a basic catalyst.

The preparation process may be illustrated by the following equation:

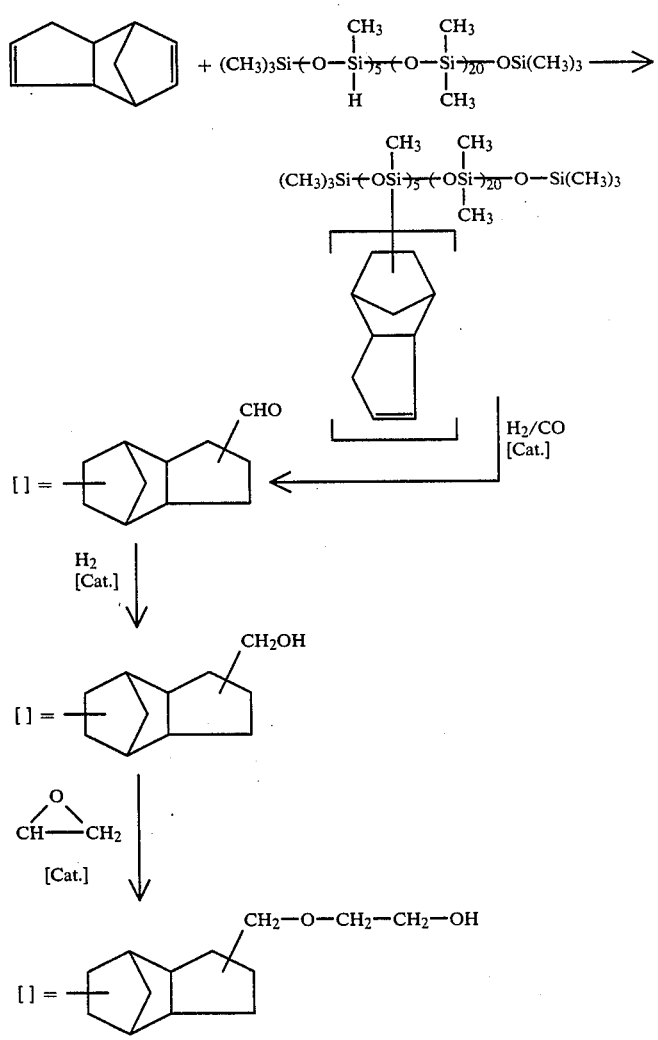

Poly-hydrogensiloxanes (XVII) are commercially available and can be prepared, for example, by equilibrating hexaorganodisiloxanes with tetrahydrogen-tetraorgano-cyclosiloxanes and, if appropriate, octaorgano-cyclotetrasiloxanes. The following poly-hydrogensiloxanes may be mentioned as examples:

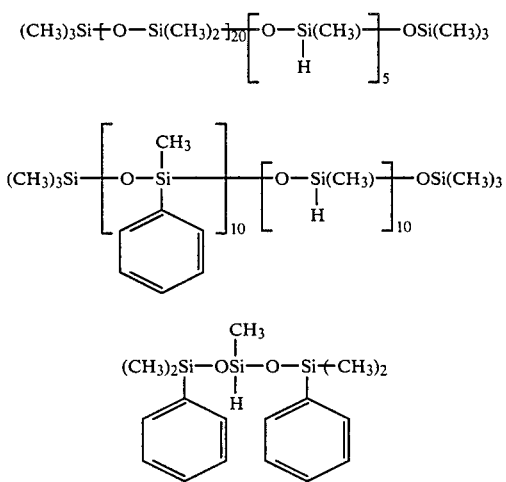

The hydrosilylation and all subsequent reaction stages to form the derivatives according to the invention can be carried out analogously to the process which yields α,ω-bis[hydroxy(alkylenoxy)methyl-tricyclo[5.2.1.0$^{2.6}$]-decenyl]-siloxanes.

The following poly[hydroxy(alkylenoxy)methyl-tricyclo-[5.2.1.0$^{2.6}$]-decanyl]-siloxane derivatives may be mentioned as examples:

The (meth)acrylates (I) according to the invention are obtained from the hydroxyl compounds of the formula (II) by esterification with (meth)acrylic acid, or the reactive derivatives (III) thereof, or by reacting with isocyanatoalkyl (meth)-acrylates (V), or by reacting with products of the 1:1 addition of diisocyanates (V) and hydroxyalkyl (meth)acrylates (VI).

For the esterification, (meth)-acrylic acid, (meth)acrylyl chloride, (meth)-acrylic anhydride or, for example, esters, such as methyl or ethyl (meth)acrylate, can be employed. The esterification is preferably carried out with (meth)acrylic acid in the presence of an acid catalyst, for example p-toluenesulphonic acid, sulphuric acid or ion exchangers in the H$^+$ form, in a solvent which is immiscible with water, for example toluene, chloroform, xylene etc.

The esterification can be carried out, for example, as follows:

The hydroxyl compound (II) and an excess of (meth)-acrylic acid are dissolved in the solvent, and the acid catalyst and a polymerization inhibitor are added. The water formed during the esterification is removed from the equilibrium by azeotropic distillation. The reaction is generally carried out in the temperature range 50° C. to about 120° C.

Suitable polymerization inhibitors are, for example, 2,6-di-tert.-butyl-4-methyl-phenol, methylene blue and hydroquinone in an amount from 0.01 to 1% by weight.

When the esterification is complete, unreacted (meth)acrylic acid is removed by extracting with a basic aqueous solution. The inhibitor is removed, for example, by adding adsorbents. The reaction products according to the invention are isolated by removing the solvents by distillation.

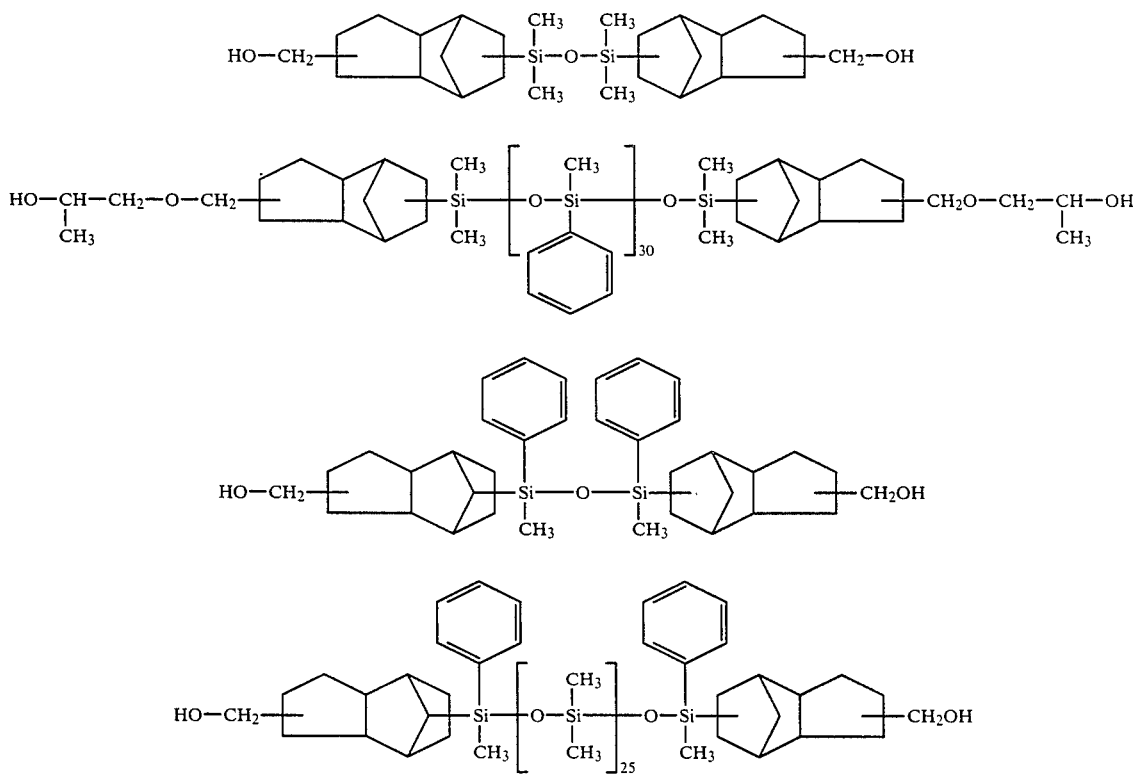

It is also possible to carry out the esterification of the hydroxyl compound (II) with (meth)-acrylyl chloride in the presence of tertiary amines, such as pyridine, triethylamine, dicyclohexylmethylamine, p-dimethylaminopyridine, tri-n-butylamine, N-methylpiperidine, cyclohexyldimethylamine etc. in inert solvents.

1.0 to 1.5 moles of (meth)-acrylyl chloride, relative to each mol of hydroxyl groups, are preferably employed. The tertiary amine is added in the equivalent amount to the OH groups of (II). The reaction is preferably carried out under anhydrous conditions in the presence of 0.01 to 1% by weight of one of the abovementioned polymerization inhibitors. Suitable solvents are those which do not react with (meth)acrylyl chloride. Examples which may be mentioned are: dichloromethane, chloroform, toluene, n-hexane, methylcyclohexane, xylene, acetone etc.

The reaction is generally carried out in the temperature range 0° to 80° C., preferably 10° to 50° C.

When the reaction is complete, the precipitated hydrochloride of the tertiary amine is filtered off, and the filtrate is washed with aqueous mineral acids, aqueous alkali metal hydrogen carbonate, or alkali metal hydrogen carbonate solution and water. After purifying the dried solution using activated charcoal, Celite, bleaching earth or other adsorbents, the compounds according to the invention are isolated, for example, by removing the solvents by distillation in vacuo.

It is furthermore possible to carry out the esterification of (II) with (meth)acrylates in the presence of transesterification catalysts, such as tetrabutoxytitanium, tetra(isopropoxy)titanium etc., the alcohol on which the (meth)acrylate is based being removed from the equilibrium by distillation.

Isocyanates (IV) (isocyanatoalkyl (meth)acrylates) are employed for the reaction of the hydroxyl compounds (II) to form urethane.

The isocyanates (IV) are commercially available or can be prepared, for example, by reacting 5,6-dihydrooxazines with phosgene (DE-OS (German Published Specification) No. 3,338,007), or by phosgenating the appropriate amino compounds (U.S. Pat. No. 2,821,544).

The following isocyanates may be mentioned as examples: 2-isocyanatoethyl methacrylate, 3-isocyanato-1,2-dimethylpropyl methacrylate, 3-isocyanatopropyl methacrylate and 3-isocyanatopropyl acrylate.

The process according to the invention is generally carried out, with exclusion of water, in an inert solvent. Examples which may be mentioned are chloroform, tetrahydrofuran, acetone, dioxane, dichlormethane, toluene and acetonitrile. Preferred solvents are chloroform, toluene and dichloromethane.

The process according to the invention is generally carried out in the temperature range 20° to 200° C., preferably 30° to 70° C.

The process according to the invention is generally carried out at atmospheric pressure. However, it is also possible to carry out the process in the pressure range 1 to 15 bar.

The reaction according to the invention to form urethane is preferably carried out with exclusion of water (preferably less than 0.1% of water).

In order to accelerate the reaction, tincontaining catalysts, such as dibutyltin dilaurate, tin(II) octoate or dibutyltin dimethoxide, are preferably used.

It is also possible to employ as catalysts compounds having tertiary amino groups, or titanium compounds. The following catalysts may be mentioned as examples: diazabicyclo[2.2.2]octane, triethylamine, N-methylpiperidine, tetrabutoxy-titanium (Ullmann, Encyclopä die der technischen Chemie [Encyclopedia of Industrial Chemistry], vol. 19, p. 306 (1981)).

In general, the catalyst is employed in an amount from 0.01 to 2.5% by weight, preferably 0.1 to 1.5% by weight, relative to the total amount of reactants.

The reaction to form urethane is generally carried out in the presence of 0.01 to 0.2% by weight of a polymerization inhibitor, for example 2,6-di-tert.-butyl-4-methylphenol.

The process according to the invention can be carried out, for example, as follows:

The reactants are dissolved in the solvent, and the catalyst is added with stirring. The course of the reaction with time can be followed, for example, by measuring the IR spectra. On complete reaction of the isocyanate groups, the reaction products are isolated by removing the solvent. Prior purification with the aid of absorbents, for example with activated charcoal, bleaching earth, silica gel or aluminum oxide, is, of course, also possible.

The reaction with acrylic acid derivatives can be carried out in an analogous fashion.

For the reaction of the hydroxyl compounds (II) to form urethane methacrylate, products of the addition of 1 mole of a diisocyante (V) to 1 mole of a hydroxyalkyl (meth)acrylate (VI) can also be employed.

Diisocyanates of the formula (V) are known per se and can be prepared, for example, by reacting diamines with phosgene. The following diisocyanates may be mentioned as examples: hexamethylene diisocyanate, trimethylhexamethylene diisocyanate, isophorone diisocyanate, 1,4-diisocyanato-cyclohexane, 1-isocyanato-4-methyl-4-isocyanato-cyclohexane, 3(4),8-bis-(isocyanatomethyl)tricyclo[$5.2.1.0^{2,6}$]decane, 2,4-diisocyanatotoluene and 1,5-diisocyanatonaphthalene.

Hydroxyalkyl (meth)acrylates of the formula (VI) are known per se and can be obtained, for example, by partial esterification of appropriate polyols. The following hydroxyalkyl (meth)acrylates may be mentioned as examples: 2-hydroxyethyl acrylate, 2-hydroxypropyl methacrylate, glycerol dimethacrylate, 1-methacryloyloxy-3-acryloyloxy-propan-2-ol, trimethylolpropane dimethacrylate and dipentaerythrite pentaacrylate.

The preparation of the addition compounds from 1 mole of a diisocyanate (V) and 1 mole of a hydroxyalkyl (meth)acrylate (VI) is carried out in a fashion which is known per se by reacting the two reactants in the molar ratio 1:1 to 10:1 and, when using excess diisocyanate, by subsequent purification of the isocyanatourethane produced.

The adduct of (V) and (VI) is preferably purified by extracting with aliphatic solvents having boiling points below 120° C. at atmospheric pressure, for example pentane, n-hexane or isopentane.

The addition compounds are generally prepared in an inert solvent. Examples which may be mentioned are acetone, chloroform, tetrahydrofuran, dioxane, methylene chloride, toluene and acetonitrile. Chloroform, toluene, acetonitrile and acetone are particularly preferred.

The process according to the invention can be carried out, for example, as follows:

The (meth)-acrylate of the formula (VI) and, if appropriate, the polymerization inhibitor are dissolved in the inert solvent and added dropwise with stirring to the diisocyanate (V), if appropriate dissolved. In this procedure, the catalyst is added to one of the two reactants. The reactants are reacted in the V:VI molar ratio of about 1:1 to 10:1, and the reaction is continued to complete conversion of the OH groups or to corresponding conversion of the isocyanate groups. The reaction of the isocyanate groups can be checked in a known fashion by IR spectroscopy and/or titration.

An excess of diisocyanate can subsequently be extracted with n-hexane, n-pentane or other aliphatic solvents having a boiling point below 120° C. (at atmospheric pressure).

In the second stage of the process according to the invention, the isocyanatourethane obtained in the first stage, if appropriate after extraction of any excess diisocyanate which may be present, is reacted with the hydroxyl compound (II) in a manner such that the number of hydroxyl equivalents corresponds to the number of NCO equivalents still present.

The reaction is generally continued until complete conversion so that neither free isocyanate nor free II remain in the reaction mixture. When the reaction is complete, the reaction product is isolated by removing the solvent. Prior filtration or purification with the aid of adsorbents, for example activated charcoal, bleaching earth, silica gel or aluminum oxide, is possible.

In general, a mixture of urethane group-containing (meth)-acrylic acid derivatives, which can be separated on adsorbents, is produced by the process according to the invention.

It is also possible to exchange the sequence of the first and second stages of the abovementioned process. In this case, diisocyanate V and hydroxyl compound II are reacted in the first stage in the NCO:OH molar ratio 2 to 4, preferably in the NCO:OH molar ratio 2.0 to 2.3, until all the hydroxyl groups in the urethane groups have reacted.

Any excess of diisocyanate (if this has been employed in excess) which may be present is subsequently extracted with the solvents mentioned in the fashion described above. The NCO groups remaining are than reacted, in the second stage, with a hydroxyalkyl (meth-)acrylate VI to form the (meth)acrylate I according to the invention, a stoichiometric equivalence of NCO and OH groups existing.

However, it is certainly possible, with the aid of diisocyanates having different reactivity of the NCO group, to prepare selectively the urethane group-containing (meth)acrylic acid derivatives of the formula I according to the invention. Diisocyanates which are suitable for this are above all those which have, besides a sterically unhindered, aliphatically bonded isocyanate group, a sterically hindered, cycloaliphatically bonded isocyanate group. Examples which may be mentioned are 1-isocyanato-1-methyl-4-isocyanatomethyl-cyclohexane, and preferably isophorone diisocyanate etc.

When these diisocyanates are used, different reaction rates naturally arise for the first and second synthesis stage, so that an NCO:OH stoichiometry of 2.0:1 to 2.05:1 is preferred in the first stage.

It is not necessary to separate the reaction mixtures obtained for use of the new urethane (meth)acrylates according to the invention in the dental field.

The (meth)-acrylates, according to the invention, of siloxanes containing tricyclodecane groups can be used as monomers for the preparation of polymeric materials. The polymerization can be carried out in a fashion known per se by free-radical initiation, and produces polymers which have a high crosslinking density.

The (meth)-acrylates, according to the invention, of siloxanes containing tricyclodecane groups can be used, in particular, as monomers for dental materials from which molded dental elements are prepared by polymerization. Dental materials which may be mentioned are, for example, filling materials for teeth, coating agents for teeth, and components for the production of tooth replacements. Depending on the area of application, dental materials may contain further auxiliaries.

The dental materials according to the invention generally contain, as polymerizable compounds (monomers), 30 to 100% by weight, preferably 60 to 100% by weight, of (meth)-acrylates of siloxanes containing tricyclodecane groups.

For use as monomers for dental filling materials or coating agents (dental varnishes) in the dental field, the (meth)-acrylates, according to the invention, of siloxanes containing tricyclodecane groups can be mixed with comonomers which are known per se. Thus, for example, the viscosity can be matched to the application. These monomer mixtures generally have a viscosity in the range 60 to 10,000 mPas.

The following comonomers may be mentioned as examples:

Triethylene glycol dimethacrylate, tetraethylene glycol dimethacrylate, 1,12-dodecanediol dimethacrylate, 1,6-hexanediol dimethacrylate, diethylene glycol dimethacrylate, 2,2-bis(p-(2'-hydroxy-3'-methacryloyloxypropoxy)-phenyl)propane, 2,2-bis(p-(2'-methacryloyloxyethoxy)-phenyl)propane, trimethylolpropane tri(meth)-acrylate, bis-((meth)acryloyloxyethoxymethyl)-tricyclo[5.2.1.0$^{2.6}$]decane (according to DE-OS (German Published Specifications) Nos. 2,931,925 and 2,931,926), 1,3-di((meth)acryloyloxypropyl)-1,1,3,3-tetra-methyldisiloxane and 1,3-bis(3-(meth)acryloyloxyethylcarbamoyloxy-propyl)-1,1,3,3-tetramethyl-disiloxane. In particular, comonomers are preferred which have a boiling point above 100° C. at 13 mbar.

In the context of the present invention, it is likewise preferred that mixtures of different (meth)acrylates according to the invention be employed.

It is also possible to employ monomer mixtures which contain several comonomers.

The (meth)-acrylates according to the invention, if appropriate as a mixture with known monomers, can be cured to form crosslinked polymers using methods which are known per se (G. M. Brauer, H. Argentar, Am. Chem. Soc., Symp. Ser. 212, pp. 359–371 (1983)). For so-called redox polymerization, a system comprising a peroxidic compound and a reducing agent, for example based on tertiary aromatic amines, is suitable. Examples of peroxides are:

Dibenzoyl peroxide, dilauroyl peroxide and di-4-chlorobenzoyl peroxide.

Examples of tertiary aromatic amines which may be mentioned are N,N-dimethyl-p-toluidine, bis-(2-hydroxyethyl)-p-toluidine, bis(2-hydroxyethyl)-3,5-dimethylaniline and N-methyl-N-(2-methyl-carbamoyloxypropyl)-3,5-dimethylaniline, described in German Patent Specification No. 2,759,239.

The concentration of the peroxide or of the amine are advantageously selected so that they are 0.1 to 5% by weight, preferably 0.5 to 3% by weight, relative to the monomer mixture. The peroxide- and amine-containing monomer mixtures are stored separately until used.

Polymerization of the monomers according to the invention can also be induced by irradiation with UV light or visible light (for example in the wavelength range 230 to 650 nm). Suitable initiators for the photo-initiated polymerization are, for example, benzil, benzil dimethyl ketal, benzoin monoalkyl ether, benzophenone, p-methoxybenzophenone, fluorenone, thioxanthone, phenanthrenequinone and 2,3-bornandione (camphorquinone), if appropriate in the presence of synergistically acting photoactivators, such as N,N-dimethylaminoethyl methacrylate, triethanolamine or 4-N,N-dimethylaminobenzenesulphonic bisallylamide.

The execution of the photopolymerization process is described, for example, in DE-A No. 3,135,115.

Besides the initiators described above, light-screening agents and polymerization inhibitors which are known per se for this application can be added to the (meth)-acrylates according to the invention.

The light-screening agent and the polymerization inhibitor are each generally employed in an amount from 0.01 to 0.50 parts by weight, relative to 100 parts by weight of the monomer mixture. The monomer mixtures can be employed, without addition of fillers, as coating agents (dental varnishes).

When used as dental filling materials, fillers are generally added to the monomer mixtures obtained. In order to be able to achieve a high degree of filling, monomer mixtures which have a viscosity in the range 60 to 10,000 mPas are particularly advantageous. Inorganic fillers can advantageously be added to the monomer mixtures containing the compounds of the formula I according to the invention. Examples which may be mentioned are mountain crystal, quartzite, cristobalite, quartz glass, highly disperse silicic acid, aluminum oxide and glass ceramics, for example lanthanum- and zirconium-containing glass ceramics (DE-A No. 2,347,591).

The inorganic fillers are preferably treated beforehand with an adhesion promoter in order to improve bonding to the polymer matrix of the molded dental element. The adhesion promotion can be achieved, for example, by treatment with organosilicon compounds (E. P. Plueddemann, Progress in Organic coatings, 11, 297 to 308 (1983)). 3-Methacryloyloxypropyl-trimethoxysilane is preferably employed.

The fillers for the dental filling materials according to the invention generally have an average particle diameter of 0.01 to 100 μm, preferably 0.05 to 50 μm, particularly preferably 0.05 to 5 μm. It can also be advantageous to employ alongside one another several fillers which have different particle diameters and different degrees of silanization.

The proportion of filler in the dental filling materials is generally 5 to 85% by weight, preferably 50 to 80% by weight.

For the preparation of the dental filling materials, the components are processed using commercially available compounders.

The proportion of the (meth)-acrylates according to the invention in the filling materials is generally 10 to 90% by weight, preferably 45 to 85% by weight, relative to the filling material.

The (meth)-acrylates, according to the invention, of siloxanes containing tricyclodecane groups can also be employed as components for the production of tooth replacements.

In this case, the monomers according to the invention are combined with the conventionally used components which are known per se. The monomers are preferably employed as a mixture with alkyl methacrylates, such as methyl methacrylate. In addition, bead polymers which are known per se can also be added. In order to adjust the tooth color, known inorganic and organic colored pigments and opacifiers can be added. The use of stabilizers and light-screening agents is also possible.

Plastic teeth are produced by free-radical polymerization of the dental materials with shaping. Processing is possible both by injection processes and compression processes and is generally carried out according to conventional production methods for teeth based on poly(methylmethacrylate), for example by thermal polymerization using polymerization initiators which are known per se, for example based on peroxides and azo compounds, such as dibenzoyl peroxide, dilauroyl peroxide, cyclohexyl percarbonate and azoisobutyrodinitrile. Mixtures of polymerization initiators having various decomposition temperatures are also highly suitable.

The plastics prepared using the (meth)-acrylates, according to the invention, of tricyclo[$5.2.1.0^{2,6}$]decanylsiloxane derivatives have a very low polymerization shrinkage, low absorbence of water, very good mechanical properties and markedly improved abrasion resistance compared to known (meth)-acrylates which are used in dental materials. Besides these advantages, the very low viscosity of the pure monomers is surprising.

EXAMPLES

EXAMPLE 1

1,3-Bis(tricyclo[$5.2.1.0^{2,6}$]dec-3-en-8(9)-yl)-1,1,3,3-tetramethyldisiloxane Synthetic route A $10^{-4}$ mol of platinum, in the form of the Lamoreaux catalyst according to U.S. Pat. No. 3,220,972, are added to a solution of 924 g of distilled dicyclopentadiene in 2 liters of chlorobenzene. 469 g of 1,1,3,3-tetramethyldisiloxane are slowly added dropwise with vigorous stirring to the reaction solution, warmed to 80° C., where the temperature of the mixture should not exceed 100° C. When the addition is complete, the decrease in intensity of the SiH bands is followed by IR spectroscopy. When the reaction is complete (about 24 hours at 100 to 120° C.), the mixture is cooled and freed of solvent in a water-pump vacuum. After addition of 500 ppm of hydroquinone monomethyl ether, the residue is fractionated in a high vacuum. In addition to a small initial fraction of unreacted dicyclopentadiene and an intermediate fraction, which contains the monoadduct of the disiloxane as the main component, 1,091 g of the bisadduct are obtained. The product is a colorless, low-viscosity liquid and represents a mixture of endo and exo isomers. Yield: 78%

Boiling point (0.07 mm of Hg): 155° to 160° C.

Synthetic route B (1) 68.9 g of dicyclopentadiene and $5.10^{-5}$ mol of platinum in the form of the Lamoreaux catalyst are dissolved in 780 ml of chlorobenzene and warmed to 80° C. 59.5 g of chlorodimethylsilane are added dropwise at this temperature. When the addition is complete, the mixture is stirred for 24 hours at 120° C. and subsequently distilled.

38 g of 8(9)-(chlorodimethylsilyl)-tricyclo[5.2.1.0$^{2.6}$]-dec-3-ene are obtained.

Boiling point (0.12 mm of Hg): 80° to 85° C.

(2) 8.9 g of 8(9)-(chlorodimethylsilyl)-tricyclo[5.2.1.0$^{2.6}$]dec-3-ene are dissolved in 50 ml of toluene. 1.2 g of methanol and 3.7 g of triethylamine are simultaneously added dropwise at room temperature. The mixture is stirred for a further 1 hour at 40° C., and, after removal of the solvent and separation of the triethylamine hydrochloride, the residue is fractionated in vacuo.

Yield: 8.5 g of 8(9)-(methoxydimethylsilyl)-tricyclo[5.2.1.0$^{2.6}$]dec-3-ene

Boiling point (0.12 mm of Hg): 88° to 91° C.

(3) Hydrolysis 10 mmol of 8(9)-(methoxydimethylsilyl)-tricyclo[5.2.1.0$^{2.6}$]dec-3-ene or 10 mmol of 8(9)-(chlorodimethylsilyl)-tricyclo[5.2.1.0$^{2.6}$]dec-3-ene are dissolved in 50 ml of ether and added dropwise to 100 ml of 0.01 N hydrochloric acid or 100 ml of saturated sodium hydrogen carbonate solution. The mixture is stirred for a further 2 hours at room temperature, and the organic phase is separated off. The disiloxane solution is washed until neutral, dried and freed of solvent. According to the analytical data, the product is identical to the 1,3-bis(tricyclo[5.2.1.0$^{2.6}$]dec-3-en-8(9)-yl)-1,1,3,3-tetramethyldisiloxane obtained by synthetic route A.

EXAMPLE 2

1,3-Bis[3(4)-(hydroxymethyl)tricyclo[5.2.1.0$^{2.6}$]decan-8(9)-yl]-1,1,3,3-tetramethyl-disiloxane 244 g of the disiloxane from Example 1 are dissolved in 700 ml of toluene. 1 g of a hydroformylation catalyst (5% Rh on aluminum oxide) is added. The suspension is transferred into a stirred autoclave and reacted with a (1:1) $H_2/CO$ mixture at 140° C. and 180 to 200 bar. The reaction is complete after 2.5 hours. The catalyst is filtered off, and the filtrate is treated, if necessary, with activated charcoal and filtered. The solvent is removed in vacuo. The $^1H$ NMR spectrum of the residue shows no olefinic protons. According to analysis by gas chromatography, the product contains the dialdehyde with a proportion of >98%.

For reduction, 200 g of the crude product are dissolved in 500 ml of ethanol and 2 ml of triethylamine are added. 10 g of Raney nickel and subsequently 0.5 ml of a 0.1% strength solution of hexachloroplatinic acid in isopropanol are then added. The mixture is hydrogenated for 3 hours in a stirred autoclave at 120° C. and a hydrogen pressure of 100 bar. The hydrogenation is checked by IR spectroscopy. If necessary, the mixture is subsequently hydrogenated until the carbonyl band in the IR spectrum is no longer present.

After filtration through activated charcoal and removal of the solvent, the product is obtained in virtually quantitative yield as a viscous, colorless residue.

The diol is readily soluble in toluene and polar solvents such as alcohols, acetone, chlorinated hydrocarbons and ethyl acetate.

Boiling point (0.05 mm of Hg): 220°–230° C.

| Molecular weight (osmometric): | | | |
|---|---|---|---|
| found 475 | | | |
| calc. 462 | | | |
| Elemental analysis | | | IR (film on KBr): |
| | C(%) | H(%) | |
| calc. | 67.53 | 9.96 | 3600–3200 cm$^{-1}$ V(O—H) |
| found | 67.8 | 10.0 | 1000–1100 cm$^{-1}$ V(C—O) and |
| OH number: 238 mg of KOH/g | | | V(Si—O—Si) |
| | | | 1250 cm$^{-1}$ V (Si—CH$^3$) |

EXAMPLE 3

1,3-Bis[3(4)(methacryloyloxymethyl)-tricyclo[5.2.1.0$^{2.6}$]decan-8(9)-yl]-1,1,3,3-tetramethyl-disiloxane 492.5 g of the product from Example 2 are dissolved in 1,000 ml of dry dichloromethane. After addition of 247.7 g of distilled triethylamine and 383 mg of 2,6-di-tert.-butyl-4-methyl-phenol, 257.5 g of freshly distilled methacrylyl chloride are added dropwise at 10° C. When the addition is complete, the mixture is stirred for a further 6 hours at room temperature. The mixture is subsequently filtered. The filtrate is washed with saturated sodium hydrogen carbonate solution, with 10% strength hydrochloric acid solution, and subsequently with water until the aqueous phase is neutral. The organic phase, dried over sodium sulphate, is stirred with activated charcoal, filtered and then filtered through silica gel 60. The filtrate is concentrated in vacuo to constant weight. 503 g of the dimethacrylate are obtained as a low-viscosity, colourless liquid ($\eta 25°$ C.=803 mPas).

Hydroxyl number: <5 mg of KOH/g.

EXAMPLE 4

Bis-methacrylate of the product of the condensation of 1 mol of the diol from Example 2 and 2 mol of ethylene oxide (A) Preparation of the condensate 462 g of 1,3-bishydroxymethyl-tricyclo[5.2.1.0$^{2.6}$]decanyl-1,1,3,3-tetramethyldisiloxane (mixture of isomers) and 600 g of toluene are placed in a heatable stirred autoclave which is provided with a device for azeotropic dehydration, and the air is replaced by nitrogen. 2.9 g of a 50% strength aqueous potassium hydroxide solution are added at 80° C. 88 g of ethylene oxide are subsequently slowly metered in at 100° to 115° C. and 0.4 to 0.6 bar, and the mixture is stirred for a further 3 hours at 100° to 105° C. The reaction product is neutralized using 29 g of water and 10.2 g of 12.5% strength aqueous sulphuric acid. After addition of a filtration auxiliary and an antioxidant (0.05% of 2,6-bis-t-butyl-p-cresol), the water is subsequently removed by distillation in vacuo at 70° to 90° C., and the salts deposited are filtered off together with the filtration auxiliary.

The neutral product is freed of about 1 g of volatile components by vacuum distillation to an internal temperature of 150° C.

Molecular weight: 545

Hydroxyl number: 208 mg of KOH/g.

Acrylate of product A:

200 g of product A are dissolved in 500 ml of toluene. 0.125 g of Ionol and 75.7 g of triethylamine are added, and 67.9 g of acrylyl chloride are added dropwise at room temperature. After 24 hours at room temperature, the product is isolated analogously to Example 3.

Yield: 191 g.
Viscosity: (25° C.) ~300 mPas.
Hydroxyl number: <2 mg of KOH/g.

EXAMPLE 5

1,3-Bis[(2-methacryloyloxyethyl)-1-carbamoyloxymethyl-tricyclo(5.2.1.0$^{2.6}$)decan-8(9)-yl]-1,1,3,3-tetramethyldisiloxane 21.1 g of the product from Example 2 are dissolved in 100 ml of chloroform which has been distilled over P$_4$O$_{10}$. After addition of 20 mg of 2,6-di-tert.-butyl-4-methylphenol and 0.1 g of tin octoate, 14.16 g of 2-isocyanatoethyl methacrylate are added dropwise. The mixture is stirred at 50° C. until the NCO groups (check by IR spectroscopy) have reacted completely (after about 15 hours). After removal of the solvent, a colorless oil is obtained in a quantitative yield.

| IR spectrum (film on KBr): | |
|---|---|
| 3200 to 3500 cm$^{-1}$ | V(N—H) |
| 1710 to 1720 cm$^{-1}$ | V(C=O), ester + amide I |
| 1640 cm$^{-1}$ | V(C=C) |
| 1510 cm$^{-1}$ | amide II |
| 1265 cm$^{-1}$ | Si—CH$_3$ |
| 1050 cm$^{-1}$ | Si—O—Si |

EXAMPLE 6

1,3-Bis-[3(4)-(acryloyloxymethyl)-tricyclo[5.2.1.0$^{2.6}$]decan-8(9)-yl]-1,1,3,3-tetramethyldisiloxane 300 g of the product from Example 2 are dissolved in 500 ml of dichloromethane (distilled over P$_4$O$_{10}$). After addition of 222 mg of 2,6-di-tert.-butyl-4-methylphenol and 158 g of freshly distilled triethylamine, 145 g of acrylyl chloride are added dropwise at 10° C. When the addition is complete, the mixture is stirred for 6 hours at room temperature. The reaction batch is worked up analogously to Example 3. 317 g of the diacrylate are obtained. The ester is colorless and has a comparable viscosity to the methacrylate from Example 3.

| Elemental analysis: | | | | |
|---|---|---|---|---|
| % | C | H | Si | O |
| calc. | 67.4 | 8.8 | 9.8 | 14.0 |
| found | 67.8 | 8.9 | 9.6 | 13.7 |

| Molecular weight (osmometric) | |
|---|---|
| calc. | 570 |
| found | 562 |

EXAMPLE 7

Preparation of a urethane methacrylate 72.73 g of hexamethylene diisocyanate and 0.2 g of dibutyltin dilaurate are dissolved in 100 ml of chloroform and warmed to 40° C. A mixture of 0.14 g of 2,6-di-tert.-butyl-4-methyl-phenol and 98.7 g of glycerol dimethacrylate is slowly added dropwise at this temperature. When half the NCO equivalents have reacted (NCO determination by reaction with dibutylamine and back titration of the excess dibutylamine with 0.1 N hydrochloric acid), 100 g of bis-(tricyclo[5.2.1.0$^{2.6}$]decan-8(9)-yl)-1,1,3,3-tetramethyl-disiloxane, dissolved in 200 ml of chloroform, are added dropwise. The mixture is stirred at 40°–60° C. until complete conversion of the NCO groups. After addition of triethylene glycol dimethacrylate, the product is freed of solvent, so that a monomer mixture containing 72 percent by weight of the methacrylate according to the invention is produced.

USE EXAMPLES

EXAMPLE 8

Preparation of a dental filling material

A monomer solution which has the following composition is prepared.

| Compound | Parts by weight |
|---|---|
| Monomer from Example 3 | 100 |
| N,N—diallyl-p-dimethylaminobenzene-sulphonamide | 0.05 |
| 2,3-bornandione | 0.2 |
| benzil dimethyl ketal | 0.125 |

The monomer solution is cured by irradiation with a commercially available dental lamp (Translux$^R$) and an exposure duration of 60 seconds to form a colorless plastic which, compared to known dental materials, has a markedly improved abrasion resistance.

The monomer solution can be used as a dental varnish.

EXAMPLE 9

Preparation of a dental filling material which hardens under the action of light 0.1 part by weight of Tinuvin P is added to 45 parts by weight of the monomer solution from Example 8.

This mixture is processed to a paste in vacuo in a Duplex compounder with 55 parts by weight of a pyrogenic silicic acid (specific surface area: 50 m$^2$/g) which has been silanized with 5% of 3-methacryloyloxypropyltrimethoxysilane.

The material obtained can be hardened to form a molded element by irradiation with a dental lamp using visible light (60 seconds).

EXAMPLE 10

A monomer solution is prepared analogously to Example 8, but the urethane methacrylate from Example 5 is used in place of the monomer from Example 3.

A flexural strength of 64 N/mm$^2$ and a flexural modulus of 1,852 N/mm$^2$ are measured on a light-hardened sample of this monomer solution. (Test according to DIN 13 922). The diametral tensile strength is 35 N/mm$^2$.

An improved abrasion resistance is also produced in the case of this plastic. It is particularly suitable as a dental filling material.

EXAMPLE 11

Preparation of a dental filling material which hardens under the action of light A solution is prepared from 100 parts by weight of the monomer mixture from Example 7, 0.2 part by weight of camphorquinone, 0.1 part by weight of benzil dimethyl ketal and 0.5 part by weight of N,N-bisallyl-(4-N,N-dimethylamino)-benzenesulphonamide. 40 parts by weight of this mixture are processed to a paste in vacuo in a Duplex compounder with 60 parts by weight of a highly disperse silicic acid (BET surface area 50 m$^2$/g) which has been silanized with 5% of 3-methacryloyloxypropyltrimethoxysilane.

The material can be hardened into a finished dental material by exposure to a dental lamp using visible light (60 seconds).

A molded element having the following properties is obtained: flexural strength 93 N/mm² and flexural modulus 4,700 N/mm².

By using filler mixtures made from silanized highly disperse silicic acid and silanized ceramic (having an average particle diameter of about 4 μm), the mechanical properties can be adjusted, depending on the purpose of use.

What is claimed is:

1. A (Meth)-acrylate of a siloxane containing tricyclodecane groups of the formula in which
R¹ and R² each independently denote hydrogen, lower alkyl, halogen or trifluoromethyl,
R³ denotes lower alkyl, cycloalkyl, cycloalkyl-alkyl or optionally substituted aryl or aralkyl wherein the optional substituents are selected from the group consisting of lower alkyl, halogen or aryl,
Z represents the $$CH_2=C-C-O-Q(-C-CH_2O)_p-CH_2-$$

group in which
R¹² and R¹³ each independently denote hydrogen or methyl
p represents a number from 0 to 20 and
Q represents a single bond, or denotes a radical of the formula $$-W-NH-C-O-$$
$$\parallel$$
$$O$$

in which
W denotes an alkylene chain,
or denotes a radical of the formula $$-G-O-C-NH-E-NH-C-O-$$

in which
E is a divalent, straight-chain or branched aliphatic radical having 2 to 24 carbon atoms, an aromatic radical having 6 to 26 carbon atoms, an araliphatic radical having 7 to 26 carbon atoms, or a cycloaliphatic radical having 6 to 26 carbon atoms, or the aliphatic, aromatic, araliphatic and/or cycloaliphatic radicals can contain 1 or 2 oxygen bridges, or several of the aliphatic, aromatic, araliphatic and/or cycloaliphatic radicals can be connected via optionally substituted methylene groups wherein said substituents are methyl or ethyl and G denotes a divalent straight-chain or branched aliphatic hydrocarbon radical, having 3 to 15 carbon atoms, or a divalent straight-chain or branched aliphatic hydrocarbon radical having 3 to 15 carbon atoms which contains 1 to 3 oxygen bridges and said radicals can be substituted by 1 to 4 additional (meth)acryloyloxy radicals, A and B each independently represents a siloxane chain which comprises m structural elements of the formula $$-O-Si- \quad \text{and/or} \quad -O-Si-$$

and the terminal group $$-O-Si-R^{10}$$

where
R⁴, R⁵, R⁶, R⁷, R⁸ and R⁹ each independently denote lower alkyl, cycloalkyl, cycloalkyl-alkyl or optionally substituted aryl or aralkyl wherein the optional substituents are selected from the group consisting of lower alkyl, halogen or aryl,
where the radicals R⁵, R⁷, and R⁸ can also represent the group in which
R¹, R² and Z have the abovementioned meaning,
R¹⁰ represents lower alkyl, and
where the total number of structural elements m, independently of one another, represent a number from 0 to 600, and
B can also represent lower alkyl.

2. A (Meth) acrylate of a siloxane containing tricyclodecane groups, according to claim 1, in which
R¹ and R² each independently denote hydrogen, lower alkyl, halogen or trifluormethyl,
R³ denotes lower alkyl, C₅ to C₇-cycloalkyl, C₆-to C₁₃-cycloalkyl-alkyl (C₆ to C₁₃) or optionally substituted C₆ to C₁₂-aryl or C₇- to C₁₈-aralkyl wherein the optional substituents are selected from the group consisting of lower alkyl, halogen or aryl,
Z represents the $$CH_2=C-C-O-Q(-C-CH_2O)_p-CH_2-$$

group, in which
R$^{12}$ and R$^{13}$ each independently denote hydrogen or methyl
p represents a number 0 to 20, and
Q represents a single bond or denotes a radical of the formula

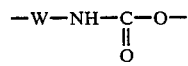

in which
W denotes an alkylene chain having 2 to 8 carbon atoms, or denotes a radical of the formula

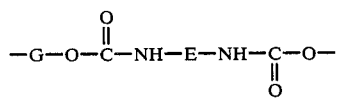

in which
E is a divalent, straight-chain or branched aliphatic radical having 2 to 12 carbon atoms, an aromatic radical having 6 to 18 carbon atoms, or a cycloaliphatic radical having 6 to 14 carbon atoms, or the aliphatic, aromatic and/or cycloaliphatic radicals can contain 1 or 2 oxygen bridges, or several of the aliphatic aromatic and/or cycloaliphatic radicals can be connected via optionally substituted methylene groups wherein said substituents are methyl or ethyl, and
G denotes a divalent straight-chain or branched aliphatic hydrocarbon radical, having 3 to 10 carbon atoms, or a divalent straight-chain or branched aliphatic hydrocarbon radical having 3 to 10 carbon atoms, said radicals can optionally be substituted by 1 to 4 additional (meth) acryloyloxy radicals,
A and B each independently represents a siloxane chain which comprises m structural elements of the formula

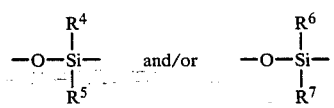

and the terminal group

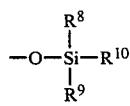

where
R$^4$, R$^5$, R$^6$, R$^7$, R$^8$ and R$^9$ each independently denote lower alkyl, C$_5$- to C$_7$-cycloalkyl, C$_6$- to C$_{13}$-cycloalkyl-alkyl or optionally substituted C$_6$- to C$_{12}$-aryl or C$_7$- to C$_{18}$-aralkyl, where the radicals R$^5$, R$^7$ and R$^8$ can also represent the

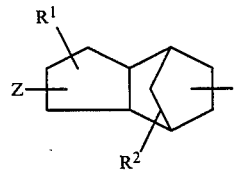

group
in which
R$^1$, R$^2$ and Z have the abovementioned meaning,
R$^{10}$ represents lower alkyl, and
where the total number of structural elements m, independently of one another, represent a number from 0 to 200, and
B can also represent lower alkyl.
3. A (Meth)-acrylate of a siloxane containing tricyclodecane groups, according to claim 1, in which
R$^1$ and R$^2$ each independently denote hydrogen or lower alkyl,
R$^3$ denotes lower alkyl, C$_5$- to C$_7$-cycloalkyl, C$_6$- to C$_{10}$-cycloalkyl-alkyl, or optionally substituted C$_6$- to C$_{11}$-aryl or C$_7$- to C$_{11}$-aralkyl wherein the optional substituents are selected from the group consisting of lower alkyl, halogen or aryl,

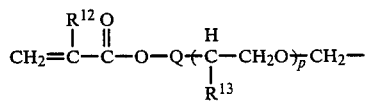

group
in which
R$^{12}$ and R$^{13}$ are identical or different and denote hydrogen or methyl,
p represents a number from 0 to 4, and
Q represents a single bond or denotes a radical of the formula

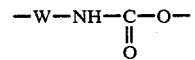

in which
W denotes an alkylene chain having 2 to 6 carbon atoms, or denotes a radical of the formula

in which
E is a divalent, straight-chain or branched aliphatic radical having 2 to 8 carbon atoms or a cycloaliphatic radical having 6 to 14 carbon atoms, and
G denotes a divalent straight-chain or branched aliphatic hydrocarbon radical, having 3 to 10 carbon atoms, or a divalent straight-chain or branched aliphatic hydrocarbon radical, having 3 to 10 carbon atoms which contains 1 oxygen bridge and said radicals can optionally be substituted by 1 or 2 additional (meth)-acryloyloxy radicals,
A and B each independently represents a siloxane chain which comprises m structural elements of the formula

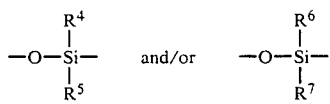

and the terminal group

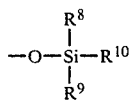

where
R$^4$, R$^5$, R$^6$, R$^7$, R$^8$, and R$^9$ each independently denote lower alkyl, C$_5$- to C$_7$-cycloalkyl, C$_6$- to C$_{10}$-cycloalkyl-alkyl, or optionally substituted C$_6$-to C$_{11}$-aryl or C$_7$- to C$_{11}$-aralkyl wherein the optional substituents are selected from the group consisting of lower alkyl, halogen or aryl, where the radicals R$^5$, R$^7$ and R$^8$ also represent the

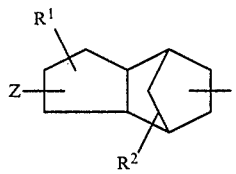

group
in which
R$^1$, R$^2$ and Z have the abovementioned meaning, R$^{10}$ represents lower alkyl, and
where the total number of structural elements m, independently of one another, represent a number from 0 to 200, and
B can also represent lower alkyl.

4. A (Meth)-acrylate of a siloxane containing tricyclodecane groups, according to claim 1, wherein 0.5 to 100 mol % of all silicon atoms are substituted by tricyclo[5.2.1.0$^{2,6}$]decanyl groups.

5. A (Meth)-acrylate of a siloxane containing tricyclodecane groups, according to claim 1, wherein the number m of structural elements is 0 to 50.

6. A process for the preparation of a (meth)-acrylate of a siloxane containing tricyclodecane groups, of the formula

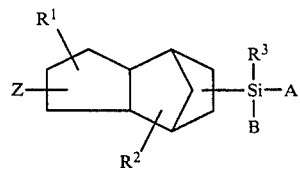

in which
R$^1$ and R$^2$ each independently denote hydrogen, lower alkyl, halogen or trifluoromethyl,
R$^3$ denotes lower alkyl, cycloalkyl, cycloalkyl-alkyl or optionally substituted aryl or aralkyl wherein the optional substituents are selected from the group consisting of lower alkyl, halogen or aryl,
Z represents the

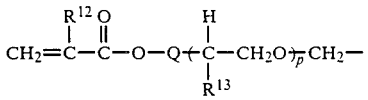

group,
in which
R$^{12}$ and R$^{13}$ each independently denote hydrogen or methyl
p represents a number 0 to 20, and
Q represents a single bond or denotes a radical of the formula

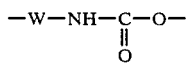

in which
W denotes an alkylene chain,
or denotes a radical of the formula

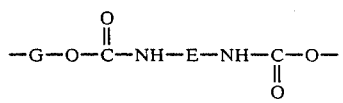

in which
E is a divalent, straight-chain or branched aliphatic radical having 2 to 24 carbon atoms, an aromatic radical having 6 to 26 carbon atoms, an araliphatic radical having 7 to 26 carbon atoms, or a cycloaliphatic radical having 6 to 26 carbon atoms, or the aliphatic aromatic, araliphatic and/or cycloaliphatic radicals can contain 1 or 2 oxygen bridges, or several of the aliphatic, aromatic, araliphatic and/or cycloaliphatic radicals can be connected via optionally substituted methylene groups wherein said substituents are methyl or ethyl and
G denotes a divalent straight-chain or branched aliphatic hydrocarbon radical 3 to 15 carbon atoms, or a divalent straight-chain or branched aliphatic hydrocarbon radical having 3 to 15 carbon atoms, which contain 1 to 3 oxygen bridges and said radicals can be optionally substituted by 1 to 4 additional (meth) acryloyloxy radicals,
A and B each independently represents a siloxane chain which comprises m structural elements of the formula

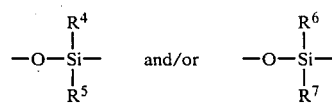

and the terminal group

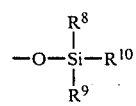

-continued

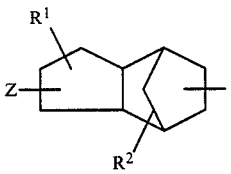

group,
in which
$R^1$, $R^2$ and Z have the abovementioned meaning,
$R^{10}$ represents lower alkyl, and where the total number of structual elements m, independently of one another, represent a number from 0 to 600, and
B can also represent lower alkyl,
wherein a poly[hydroxy(alkyleneoxy)-methyl-tricyclo[5.2.1.0$^{2.6}$]-decanyl]-siloxane of the formula

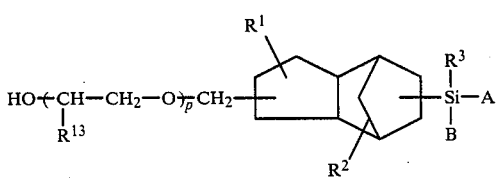

in which
$R^1$, $R^2$, $R^3$, $R^{13}$, p, A and B have the abovementioned meaning,
in the case of the preparation of compounds in which Q represents a single bond, is esterified using a (meth)acrylic acid derivative of the formula

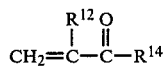

in which
$R^{12}$ has the abovementioned meaning, and
$R^{14}$ represents hydroxyl, chlorine, methoxy, ethoxy or (meth)acryloyloxy,
or in the case of the preparation of a compound in which Q represents a radical of the formula

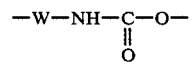

in which
W represents an alkylene chain,
is reacted with an isocyanate of the formula

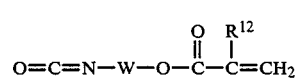

in which
$R^{12}$ and W have the abovementioned meaning, in an inert solvent,
or, in the case of the preparation of a compound in which Q represents a radical of the formula

in which

E is a divalent, straight-chain or branched aliphatic radical having 2 to 24 carbon atoms, an aromatic radical having 6 to 26 carbon atoms, an araliphatic radical having 7 to 26 carbon atoms or a cycloaliphatic radical having 6 to 26 carbon atoms, or the aliphatic aromatic, araliphatic and/or cycloaliphatic radicals can contain 1 to 2 oxygen bridges, or several of the aliphatic, aromatic, araliphatic and/or cycloaliphatic radicals can be connected via optionally substituted methylene groups, wherein said substituents are methyl or ethyl and G denotes a divalent straight-chain or branched aliphatic hydrocarbon radical, having 3 to 15 carbon atoms, as a divalent straight-chain or branched aliphatic hydrocarbon radical having 3 to 15 carbon atoms, which contain 1 to 3 oxygen bridges and said radicals can optionally be substituted by 1 to 4 additional (meth)acryloyloxy radicals, is reacted with the product of the addition reaction of 1 mole of a diisocyanate of the formula

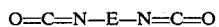

in which
E has the abovementioned meaning, and 1 mole of a hydroxyalkyl (meth)acrylate of the formula

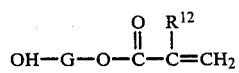

in which
G and $R^{12}$ have the abovementioned meaning, where a stoichiometric equivalence exists between the NCO groups of the adduct of the diisocyanate and the hydroxylalkyl (meth) acrylate, the siloxane and the OH groups, said reaction is conducted in an inert solvent.

7. A process according to claim 6, wherein the reaction with the (meth)acrylic acid derivative is carried out in the temperature range 0° to 120° C.

8. A process according to claim 6, wherein the reaction with the isocyanate is carried out in the presence of a catalyst and a polymerization inhibitor in the temperature range 20° to 100° C.

9. A polymer of monomer mixtures, containing (meth)-acrylates of siloxanes containing tricyclodecane groups of the formula

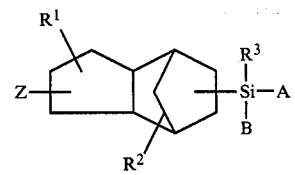

in which
$R^1$ and $R^2$ each independently denote hydrogen, lower alkyl, halogen or trifluoromethyl,
$R^3$ denotes lower alkyl, cycloalkyl, cycloalkyl-alkyl or optionally substituted aryl or aralkyl wherein the optional substituents are selected from the group consisting of lower alkyl, halogen or aryl,
Z represents the

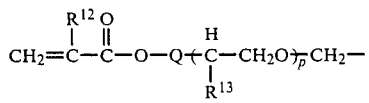

group
in which
R$^{12}$ and R$^{13}$ each independently denote hydrogen or methyl
p represents a number from 0 to 20 and
Q represents a single bond, or denotes a radical of the formula

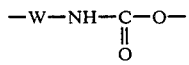

in which
W denotes an alkylene chain,
or denotes a radical of the formula

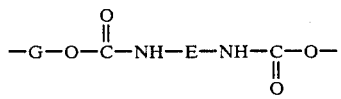

in which
E is a divalent, straight-chain or branched aliphatic radical having 2 to 24 carbon atoms, an aromatic radical having 6 to 26 carbon atoms, an araliphatic radical having 7 to 26 carbon atoms, or a cycloaliphatic radical having 6 to 26 carbon atoms, or the aliphatic aromatic, araliphatic and/or cycloaliphatic radicals can contain 1 or 2 oxygen bridges, or several of the aliphatic, aromatic, araliphatic and/or cycloaliphatic radicals can be connected via optionally substituted methylene groups wherein said substituents are methyl or ethyl and
G denotes a divalent straight-chain or branched aliphatic hydrocarbon radical, having 3 to 15 carbon atoms, or a divalent straight-chain or branched aliphatic hydrocarbon radical having 3 to 15 carbon atoms which contains 1 to 3 oxygen bridges and said radicals can be substituted by 1 to 4 additional (meth)acryloyloxy radicals,
A and B each independently represents a siloxane chain which comprises m structural elements of the formula

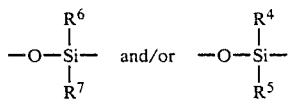

and the terminal group

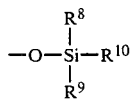

where
R$^4$, R$^5$, R$^6$, R$^7$, R$^8$ and R$^9$ each independently denote lower alkyl, cycloalkyl, cycloalkyl-alkyl or optionally substituted aryl or aralkyl wherein the optional substituents are selected from the group consisting of lower alkyl, halogen or aryl,
where the radicals R$^5$, R$^7$, and R$^8$ can also represent the

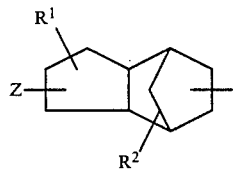

group
in which
R$^1$, R$^2$ and Z have the abovementioned meaning,
R$^{10}$ represents lower alkyl, and
where the total number of structural elements m, independently of one another, represent a number from 0 to 600, and
B can also represent lower alkyl.

* * * * *

UNITED STATES PATENT AND TRADEMARK OFFICE
CERTIFICATE OF CORRECTION

PATENT NO. : 4,843,136
DATED : June 27, 1989
INVENTOR(S) : Jürgen Reiners, et al It is certified that error appears in the above-identified patent and that said Letters Patent is hereby corrected as shown below:

Col. 18, line 1     Insert --1-- Before "+"
Col. 30, line 38    Insert --(-- before "tricyclo"
Col. 30, line 40    Correct spelling of --tricyclo--
Col. 38, line 5     Insert -- - -- after "Encyclopä--
Col. 46, line 15    Delete "0.05" and substitute --0.5--

Signed and Sealed this

Twenty-eighth Day of August, 1990

Attest:

HARRY F. MANBECK, JR.

*Attesting Officer*     *Commissioner of Patents and Trademarks*

UNITED STATES PATENT AND TRADEMARK OFFICE
CERTIFICATE OF CORRECTION

PATENT NO. : 4,843,136
DATED : June 27, 1989
INVENTOR(S) : Reiners, et al.

It is certified that error appears in the above-indentified patent and that said Letters Patent is hereby corrected as shown below:

Title Page     [30] Foreign Application Priority Data:
After " Mar. 12, 1987 " delete " [JP] Japan "
and substitute -- [DE] Fed. Rep. of Germany --

Signed and Sealed this

Twenty-seventh Day of August, 1996

Attest:

BRUCE LEHMAN

Attesting Officer     Commissioner of Patents and Trademarks